United States Patent
Chang et al.

(10) Patent No.: US 12,129,470 B2
(45) Date of Patent: Oct. 29, 2024

(54) METHODS AND COMPOSITIONS RELATED TO RNA-TARGETED RHO SMALL GTPase RND3/RhoE THERAPY

(71) Applicant: The Texas A&M University System, College Station, TX (US)

(72) Inventors: Jiang Chang, College Station, TX (US); Weijia Luo, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 17/171,288

(22) Filed: Feb. 9, 2021

(65) Prior Publication Data

US 2022/0251568 A1  Aug. 11, 2022

(51) Int. Cl.
| | | |
|---|---|---|
| C07H 21/02 | (2006.01) | |
| A61K 31/713 | (2006.01) | |
| A61K 45/06 | (2006.01) | |
| C07H 21/04 | (2006.01) | |
| C12N 15/113 | (2010.01) | |
| C12Q 1/6886 | (2018.01) | |
| G01N 33/573 | (2006.01) | |

(52) U.S. Cl.
CPC ........ C12N 15/1137 (2013.01); A61K 31/713 (2013.01); A61K 45/06 (2013.01); C12Q 1/6886 (2013.01); G01N 33/573 (2013.01); C12N 2310/14 (2013.01); C12N 2320/31 (2013.01)

(58) Field of Classification Search
CPC .......................... C12N 15/113; C12N 2310/14
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,837,028 A | 6/1989 | Allen |
| 4,920,016 A | 4/1990 | Allen et al. |
| 5,019,369 A | 5/1991 | Presant et al. |
| 2002/0086356 A1 | 7/2002 | Tuschl et al. |

OTHER PUBLICATIONS

Grise et al. (Hepatology, 55, 6, 2012, 1766-1775).*
Elbashir et al. (The EMBO Journal, vol. 20, No. 23, pp. 6877-6888, 2001).*
Altschul, Stephen F., et al. "Basic local alignment search tool." Journal of molecular biology 215.3 (1990): 403-410.
Anderson, W. French. "Prospects for human gene therapy." Science 226.4673 (1984): 401-409.
Aoki, K. et al. A RhoA and Rnd3 cycle regulates actin reassembly during membrane blebbing. Proc. Natl Acad. Sci. USA 113, E1863-E1871 (2016).
Arber, S. et al. Regulation of actin dynamics through phosphorylation of cofilin by LIM-kinase. Nature 393, 805-809 (1998).
Arthur, W. T. & Burridge, K. RhoA inactivation by p190RhoGAP regulates cell spreading and migration by promoting membrane protrusion and polarity. Mol. Biol. Cell 12, 2711-2720 (2001).
Azzarelli, R. et al. An antagonistic interaction between PlexinB2 and Rnd3 controls RhoA activity and cortical neuron migration. Nat. Commun. 5, 3405 (2014).
Bazykin, G. A. & Kochetov, A. V. Alternative translation start sites are conserved in eukaryotic genomes. Nucleic Acids Res. 39, 567-577 (2011).
Boureux, Anthony, et al. "Evolution of the Rho family of ras-like GTPases in eukaryotes." Molecular biology and evolution 24.1 (2007): 203-216.
Brummelkamp, Thijn R., René Bernards, and Reuven Agami. "A system for stable expression of short interfering RNAs in mammalian cells." science 296.5567 (2002): 550-553.
Bustin, Stephen A. "Absolute quantification of mRNA using real-time reverse transcription polymerase chain reaction assays." Journal of molecular endocrinology 25.2 (2000): 169-193.
Calvo, S. E., Pagliarini, D. J. & Mootha, V. K. Upstream open reading frames cause widespread reduction of protein expression and are polymorphic among humans. Proc. Natl Acad. Sci. USA 106, 7507-7512 (2009).
Chang, L. et al. MicroRNA-200c regulates the sensitivity of chemotherapy of gastric cancer SGC7901/DDP cells by directly targeting RhoE. Pathol. Oncol. Res. 20, 93-98 (2014).
Chardin, P. Function and regulation of Rnd proteins. Nat. Rev. Mol. Cell Biol. 7, 54-62 (2006).
Dai, Y. et al. RhoE fine-tunes inflammatory response in myocardial infarction. Circulation 139, 1185-1198 (2019).
Dai, Y., Luo, W. & Chang, J. Rho kinase signaling and cardiac physiology. Curr. Opin. Physiol. 1, 14-20 (2018).
Dornburg, Reticuloendotheliosis. "Reticuloendotheliosis viruses and derived vectors." Gene therapy 2.5 (1995): 301-310.
Eglitis, Martin A., and W. French Anderson. "Retroviral vectors for introduction of genes in to mammalian cells." Biotechniques 6.7 (1988): 608-614.
Fang, Y. N. et al. Highly expressed miR-182-5p can promote preeclampsia progression by degrading RND3 and inhibiting HTR-8/SVneo cell invasion. Eur. Rev. Med. Pharm. Sci. 22, 6583-6590 (2018).
Fiegen, D., Blumenstein, L., Stege, P., Vetter, I. R. & Ahmadian, M. R. Crystal structure of Rnd3/RhoE: functional implications. FEBS Lett. 525, 100-104 (2002).
Foster, R. et al. Identification of a novel human Rho protein with unusual properties: GTPase deficiency and in vivo farnesylation. Mol. Cell Biol. 16, 2689-2699 (1996).
Gabizon, Alberto, and Demetrios Papahadjopoulos. "Liposome formulations with prolonged circulation time in blood and enhanced uptake by tumors." Proceedings of the National Academy of Sciences 85.18 (1988): 6949-6953.

(Continued)

*Primary Examiner* — Amy Rose Hudson
(74) *Attorney, Agent, or Firm* — Meunier Carlin & Curfman LLC

(57) ABSTRACT

Disclosed are RNA inhibitors, such as small interfering RNAs (siRNAs) and short hairpin RNAs (shRNAs) specific for RND3, alternatively referred to as RhoE. Also disclosed are methods of treating subjects by administering RNA inhibitors. Further disclosed are methods of detecting potential modulators of RND3.

10 Claims, 10 Drawing Sheets

Specification includes a Sequence Listing.

(56) References Cited

OTHER PUBLICATIONS

Goh, L. L. & Manser, E. The GTPase-deficient Rnd proteins are stabilized by their effectors. J. Biol. Chem. 287, 31311-31320 (2012).

Goh, L. L. & Manser, E. The RhoA GEF Syx is a target of Rnd3 and regulated via a Raf1-like ubiquitin-related domain. PLoS ONE 5, e12409 (2010). 36. Chardin, P. Function and regulation of Rnd proteins. Nat. Rev. Mol. Cell Biol. 7, 54-62 (2006).

Guasch, R. M., Scambler, P., Jones, G. E. & Ridley, A. J. RhoE regulates actin cytoskeleton organization and cell migration. Mol. Cell Biol. 18, 4761-4771 (1998).

Hodge, R. G. & Ridley, A. J. Regulating Rho GTPases and their regulators. Nat. Rev. Mol. Cell Biol. 17, 496-510 (2016).

Ingolia, N. T., Ghaemmaghami, S., Newman, J. R. & Weissman, J. S. Genomewide analysis in vivo of translation with nucleotide resolution using ribosome profiling. Science 324, 218-223 (2009).

Jackson, R. J., Hellen, C. U. & Pestova, T. V. The mechanism of eukaryotic translation initiation and principles of its regulation. Nat. Rev. Mol. Cell Biol. 11, 113-127 (2010).

Jiang, C. et al. Epstein-Barr virus miRNA BART2-5p promotes metastasis of nasopharyngeal carcinoma by suppressing RND3. Cancer Res. 80, 1957-1969 (2020).

Jie, W. et al. Pathophysiological functions of Rnd3/RhoE. Compr. Physiol. 6, 169-186 (2015).

Jordan, P., Brazao, R., Boavida, M. G., Gespach, C. & Chastre, E. Cloning of a novel human Rac1b splice variant with increased expression in colorectal tumors. Oncogene 18, 6835-6839 (1999).

Kochetov, A. V. Alternative translation start sites and hidden coding potential of eukaryotic mRNAs. Bioessays 30, 683-691 (2008).

Kozak, M. Initiation of translation in prokaryotes and eukaryotes. Gene 234, 187-208 (1999).

Kozak, M. Structural features in eukaryotic mRNAs that modulate the initiation of translation. J. Biol. Chem. 266, 19867-19870 (1991).

Lawson, C. D. & Ridley, A. J. Rho GTPase signaling complexes in cell migration and invasion. J. Cell Biol. 217, 447-457 (2018).

Lee, Nan Sook, et al. "Expression of small interfering RNAs targeted against HIV-1 rev transcripts in human cells." Nature biotechnology 20.5 (2002): 500-505.

Lin, X. et al. Genetic deletion of Rnd3 results in aqueductal stenosis leading to hydrocephalus through up-regulation of Notch signaling. Proc. Natl Acad. Sci. USA 110, 8236-8241 (2013).

Liu, B. et al. Downregulation of RND3/RhoE in glioblastoma patients promotes tumorigenesis through augmentation of notch transcriptional complex activity. Cancer Med. 4, 1404-1416 (2015).

Liu, B. et al. RND3 promotes Snail 1 protein degradation and inhibits glioblastoma cell migration and invasion. Oncotarget 7, 82411-82423 (2016).

Luo, H. et al. Up-regulated miR-17 promotes cell proliferation, tumour growth and cell cycle progression by targeting the RND3 tumour suppressor gene in colorectal carcinoma. Biochem. J. 442, 311-321 (2012).

Madigan, J. P. et al. Regulation of Rnd3 localization and function by protein kinase C alpha-mediated phosphorylation. Biochem. J. 424, 153-161 (2009).

Maekawa, M. et al. Signaling from Rho to the actin cytoskeleton through protein kinases ROCK and LIM-kinase. Science 285, 895-898 (1999).

Marks, P. W. & Kwiatkowski, D. J. Genomic organization and chromosomal location of murine Cdc42. Genomics 38, 13-18 (1996).

McColl, B., Garg, R., Riou, P., Riento, K. & Ridley, A. J. Rnd3-induced cell rounding requires interaction with Plexin-B2. J. Cell Sci. 129, 4046-4056 (2016).

Miller, A. D. "Retrovirus Packaging Cells", Human Gene Therapy. 1: 5-14, 1990.

Miyagishi, Makoto, and Kazunari Taira. "U6 promoter-driven siRNAs with four uridine 3' overhangs efficiently suppress targeted gene expression in mammalian cells." Nature biotechnology 20.5 (2002): 497-500.

Modrek, B. & Lee, C. A genomic view of alternative splicing. Nat. Genet. 30, 13-19 (2002).

Modrek, B., Resch, A., Grasso, C. & Lee, C. Genome-wide detection of alternative splicing in expressed sequences of human genes. Nucleic Acids Res. 29, 2850-2859 (2001).

Muratcioglu, S. et al. GTP-dependent K-Ras dimerization. Structure 23, 1325-1335 (2015).

Nan, X. et al. Single-molecule superresolution imaging allows quantitative analysis of RAF multimer formation and signaling. Proc. Natl Acad. Sci. USA 110, 18519-18524 (2013).

Ongusaha, P. P. et al. RhoE is a pro-survival p53 target gene that inhibits ROCK I-mediated apoptosis in response to genotoxic stress. Curr. Biol. 16, 2466-2472 (2006).

Pacary, E. et al. Proneural transcription factors regulate different steps of cortical neuron migration through Rnd-mediated inhibition of RhoA signaling. Neuron 69, 1069-1084 (2011).

Pacary, E., Azzarelli, R. & Guillemot, F. Rnd3 coordinates early steps of cortical neurogenesis through actin-dependent and -independent mechanisms. Nat. Commun. 4, 1635 (2013).

Paddison, Patrick J., et al. "Short hairpin RNAs (shRNAs) induce sequence-specific silencing in mammalian cells." Genes & development 16.8 (2002): 948-958.

Paul, Cynthia P., et al. "Effective expression of small interfering RNA in human cells." Nature biotechnology 20.5 (2002): 505-508.

Paysan, L., Piquet, L., Saltel, F. & Moreau, V. Rnd3 in cancer: a review of the evidence for tumor promoter or suppressor. Mol. Cancer Res. 14, 1033-1044 (2016).

Rabinowitz, Joseph E., et al. "Cross-packaging of a single adeno-associated virus (AAV) type 2 vector genome into multiple AAV serotypes enables transduction with broad specificity." Journal of virology 76.2 (2002): 791-801.

Riento, K. & Ridley, A. J. Rocks: multifunctional kinases in cell behaviour. Nat. Rev. Mol. Cell Biol. 4, 446-456 (2003).

Riento, K. et al. RhoE function is regulated by ROCK I-mediated phosphorylation. EMBO J. 24, 1170-1180 (2005).

Riento, K., Guasch, R. M., Garg, R., Jin, B. & Ridley, A. J. RhoE binds to ROCK I and inhibits downstream signaling. Mol. Cell Biol. 23, 4219-4229 (2003).

Riou, P. et al. 14-3-3 proteins interact with a hybrid prenyl-phosphorylation motif to inhibit G proteins. Cell 153, 640-653 (2013).

Shi, Y. et al. Abnormal SDS-PAGE migration of cytosolic proteins can identify domains and mechanisms that control surfactant binding. Protein Sci. 21, 1197-1209 (2012).

Shirai, A. et al. Global analysis of gel mobility of proteins and its use in target identification. J. Biol. Chem. 283, 10745-10752 (2008).

Szoka Jr, Frank, and Demetrios Papahadjopoulos. "Comparative properties and methods of preparation of lipid vesicles (liposomes)." Annual review of biophysics and bioengineering 9.1 (1980): 467-508.

Tuschl T et al., "The siRNA User Guide," revised Oct. 11, 2002.

Tuschl, Thomas. "Expanding small RNA interference." Nature biotechnology 20.5 (2002): 446-448.

Villalonga, P., Guasch, R. M., Riento, K. & Ridley, A. J. RhoE inhibits cell cycle progression and Ras-induced transformation. Mol. Cell Biol. 24, 7829-7840 (2004).

Wan, J. & Qian, S. B. TISdb: a database for alternative translation initiation in mammalian cells. Nucleic Acids Res. 42, D845-D850 (2014).

Xia, W. et al. MicroRNA-200b regulates cyclin D1 expression and promotes Sphase entry by targeting RND3 in HeLa cells. Mol. Cell Biochem. 344, 261-266 (2010).

Yang, X. et al. Genetic deletion of Rnd3/RhoE results in mouse heart calcium leakage through upregulation of protein kinase A signaling. Circulation Res. 116, e1-e10 (2015).

Yi, X. et al. Histone methyltransferase Setd2 is critical for the proliferation and differentiation of myoblasts. Biochim. Biophys. Acta Mol. Cell Res. 1864, 697-707 (2017).

(56) References Cited

OTHER PUBLICATIONS

Yue, X. et al. Rnd3 haploinsufficient mice are predisposed to hemodynamic stress and develop apoptotic cardiomyopathy with heart failure. Cell Death Dis. 5, e1284 (2014).
Yue, X. et al. Rnd3/RhoE modulates hypoxia-inducible factor 1alpha/Vascular endothelial growth factor signaling by stabilizing hypoxia-inducible factor 1 alpha and regulates responsive cardiac angiogenesis. Hypertension 67, 597-605 (2016).
Zhou, J. et al. Chaperone-mediated autophagy regulates proliferation by targeting RND3 in gastric cancer. Autophagy 12, 515-528 (2016).

* cited by examiner

SEQUENCE LISTING

<160> NUMBER OF SEQ ID NOS: 37

<210> SEQ ID NO 1
<211> LENGTH: 21
<212> TYPE: RNA
<213> ORGANISM: Artificial Sequence
<220> FEATURE:
<223> OTHER INFORMATION: Synthetic construct

<400> SEQUENCE: 1
gcaaaucuau cauggauccu a                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic construct

<400> SEQUENCE: 2
gucguuuaga uaguaccuag g                                              21

<210> SEQ ID NO 3
<211> LENGTH: 21
<212> TYPE: RNA
<213> ORGANISM: Artificial Sequence
<220> FEATURE:
<223> OTHER INFORMATION: Synthetic construct

<400> SEQUENCE: 3
gcaguugcua cggacuuacg a                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic construct

<400> SEQUENCE: 4
gccgucaacg augccugaau g                                              21

<210> SEQ ID NO 5
<211> LENGTH: 48
<212> TYPE: DNA
<213> ORGANISM: Artificial Sequence
<220> FEATURE:
<223> OTHER INFORMATION: Synthetic construct

<400> SEQUENCE: 5
caaatctatc atggatccta tcaagagtag gatccatgat agatttgc                 48

<210> SEQ ID NO 6
<211> LENGTH: 49
<212> TYPE: DNA
<213> ORGANISM: Artificial Sequence
<220> FEATURE:
<223> OTHER INFORMATION: Synthetic construct

<400> SEQUENCE: 6
cgtttagata gtacctagga tagttctcat cctaggtact atctaaacg                49

<210> SEQ ID NO 7
<211> LENGTH: 48
<212> TYPE: DNA
<213> ORGANISM: Artificial Sequence -continued

```
<220> FEATURE:
<223> OTHER INFORMATION: Synthetic construct

<400> SEQUENCE: 7
cagttgctac ggacttacga tcaagagtcg taagtccgta gcaactgc                48

<210> SEQ ID NO 8
<211> LENGTH: 49
<212> TYPE: DNA
<213> ORGANISM: Artificial Sequence
<220> FEATURE:
<223> OTHER INFORMATION: Synthetic construct

<400> SEQUENCE: 8
cgtcaacgat gcctgaatgc tagttctcag cattcaggca tcgttgacg               49

<210> SEQ ID NO 9
<211> LENGTH: 49
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: (22)..(28)
<223> OTHER INFORMATION: n is a, c, g, or t

<400> SEQUENCE: 9
gcaaatctat catggatcct annnnnnnta ggatccatga tagatttgc               49

<210> SEQ ID NO 10
<211> LENGTH: 49
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: (22)..(28)
<223> OTHER INFORMATION: n is a, c, g, or t

<400> SEQUENCE: 10
cgtttagata gtacctagga tnnnnnnnat cctaggtact atctaaacg               49

<210> SEQ ID NO 11
<211> LENGTH: 48
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: (21)..(27)
<223> OTHER INFORMATION: n is a, c, g, or t

<400> SEQUENCE: 11
cagttgctac ggacttacga nnnnnnntcg taagtccgta gcaactgc                48

<210> SEQ ID NO 12
<211> LENGTH: 48
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: (21)..(27)
<223> OTHER INFORMATION: n is a, c, g, or t
```

<400> SEQUENCE: 12
gtcaacgatg cctgaatgct nnnnnnnagc attcaggcat cgttgacg        48

<210> SEQ ID NO 13
<211> LENGTH: 21
<212> TYPE: DNA
<213> ORGANISM: Artificial Sequence
<220> FEATURE:
<223> OTHER INFORMATION: Synthetic construct

<400> SEQUENCE: 13
gcaaatctat catggatcct a        21

<210> SEQ ID NO 14
<211> LENGTH: 21
<212> TYPE: DNA
<213> ORGANISM: Artificial Sequence
<220> FEATURE:
<223> OTHER INFORMATION: Synthetic construct

<400> SEQUENCE: 14
cgtttagata gtacctagga t        21

<210> SEQ ID NO 15
<211> LENGTH: 21
<212> TYPE: DNA
<213> ORGANISM: Artificial Sequence
<220> FEATURE:
<223> OTHER INFORMATION: Synthetic construct

<400> SEQUENCE: 15
gcagttgcta cggacttacg a        21

<210> SEQ ID NO 16
<211> LENGTH: 21
<212> TYPE: DNA
<213> ORGANISM: Artificial Sequence
<220> FEATURE:
<223> OTHER INFORMATION: Synthetic construct

<400> SEQUENCE: 16
cgtcaacgat gcctgaatgc t        21

<210> SEQ ID NO 17
<211> LENGTH: 21
<212> TYPE: DNA
<213> ORGANISM: Artificial Sequence
<220> FEATURE:
<223> OTHER INFORMATION: Synthetic construct

<400> SEQUENCE: 17
taggatccat gatagatttg c        21

<210> SEQ ID NO 18
<211> LENGTH: 21
<212> TYPE: DNA
<213> ORGANISM: Artificial Sequence
<220> FEATURE:
<223> OTHER INFORMATION: Synthetic construct

<400> SEQUENCE: 18
atcctaggta ctatctaaac g        21

<210> SEQ ID NO 19
<211> LENGTH: 21

```
<212> TYPE: DNA
<213> ORGANISM: Artificial Sequence
<220> FEATURE:
<223> OTHER INFORMATION: Synthetic construct

<400> SEQUENCE: 19
tcgtaagtcc gtagcaactg c                                             21

<210> SEQ ID NO 20
<211> LENGTH: 21
<212> TYPE: DNA
<213> ORGANISM: Artificial Sequence
<220> FEATURE:
<223> OTHER INFORMATION: Synthetic construct

<400> SEQUENCE: 20
agcattcagg catcgttgac g                                             21

<210> SEQ ID NO 21
<211> LENGTH: 244
<212> TYPE: PRT
<213> ORGANISM: Artificial Sequence
<220> FEATURE:
<223> OTHER INFORMATION: Synthetic construct

<400> SEQUENCE: 21
```

Met Lys Glu Arg Arg Ala Ser Gln Lys Leu Ser Ser Lys Ser Ile Met
1               5                   10                  15

Asp Pro Asn Gln Asn Val Lys Cys Lys Ile Val Val Gly Asp Ser
            20                  25                  30

Gln Cys Gly Lys Thr Ala Leu Leu His Val Phe Ala Lys Asp Cys Phe
        35                  40                  45

Pro Glu Asn Tyr Val Pro Thr Val Phe Glu Asn Tyr Thr Ala Ser Phe
    50                  55                  60

Glu Ile Asp Thr Gln Arg Ile Glu Leu Ser Leu Trp Asp Thr Ser Gly
65                  70                  75                  80

Ser Pro Tyr Tyr Asp Asn Val Arg Pro Leu Ser Tyr Pro Asp Ser Asp
                85                  90                  95

Ala Val Leu Ile Cys Phe Asp Ile Ser Arg Pro Glu Thr Leu Asp Ser
            100                 105                 110

Val Leu Lys Lys Trp Lys Gly Glu Ile Gln Glu Phe Cys Pro Asn Thr
        115                 120                 125

Lys Met Leu Leu Val Gly Cys Lys Ser Asp Leu Arg Thr Asp Val Ser
130                 135                 140

Thr Leu Val Glu Leu Ser Asn His Arg Gln Thr Pro Val Ser Tyr Asp
145                 150                 155                 160

Gln Gly Ala Asn Met Ala Lys Gln Ile Gly Ala Ala Thr Tyr Ile Glu
                165                 170                 175

Cys Ser Ala Leu Gln Ser Glu Asn Ser Val Arg Asp Ile Phe His Val
            180                 185                 190

Ala Thr Leu Ala Cys Val Asn Lys Thr Asn Lys Asn Val Lys Arg Asn
        195                 200                 205

Lys Ser Gln Arg Ala Thr Lys Arg Ile Ser His Met Pro Ser Arg Pro
    210                 215                 220

Glu Leu Ser Ala Val Ala Thr Asp Leu Arg Lys Asp Lys Ala Lys Ser
225                 230                 235                 240

Cys Thr Val Met

```
<210> SEQ ID NO 22
<211> LENGTH: 735
<212> TYPE: DNA
<213> ORGANISM: Artificial Sequence
<220> FEATURE:
<223> OTHER INFORMATION: Synthetic construct

<400> SEQUENCE: 22
aatgaaggag agaagagcca gccagaaatt atccagcaaa tctatcatgg atcctaatca     60
gaacgtgaaa tgcaagatag ttgtggtggg agacagtcag tgtggaaaaa ctgcgctgct    120
ccatgtcttc gccaaggact gcttccccga gaattacgtt cctacagtgt tgagaatta    180
cacggccagt tttgaaatcg acacacaaag aatagagttg agcctgtggg acacttcggg    240
ttctccttac tatgacaatg tccgccccct ctcttaccct gattcggatg ctgtgctgat    300
ttgctttgac atcagtagac cagagaccct ggacagtgtc ctcaaaaagt ggaaaggtga    360
aatccaggaa ttttgtccaa ataccaaaat gctcttggtc ggctgcaagt ctgatctgcg    420
gacagatgtt agtacattag tagagctctc caatcacagg cagacgccag tgtcctatga    480
ccagggggca aatatggcca acagattgg agcagctact tatatcgaat gctcagcttt     540
acagtcggaa aatagcgtca gagacatttt tcacgttgcc accttggcat gtgtaaataa    600
gacaaataaa aacgttaagc ggaacaaatc acagagagcc acaaagcgga tttcacacat    660
gcctagcaga ccagaactct cggcagttgc tacggactta cgaaaggaca agcgaagag    720
ctgcactgtg atgtg                                                     735

<210> SEQ ID NO 23
<211> LENGTH: 229
<212> TYPE: PRT
<213> ORGANISM: Artificial Sequence
<220> FEATURE:
<223> OTHER INFORMATION: Synthetic construct

<400> SEQUENCE: 23

Met Asp Pro Asn Gln Asn Val Lys Cys Lys Ile Val Val Gly Asp
1               5                   10                  15

Ser Gln Cys Gly Lys Thr Ala Leu Leu His Val Phe Ala Lys Asp Cys
                20                  25                  30

Phe Pro Glu Asn Tyr Val Pro Thr Val Phe Glu Asn Tyr Thr Ala Ser
            35                  40                  45

Phe Glu Ile Asp Thr Gln Arg Ile Glu Leu Ser Leu Trp Asp Thr Ser
        50                  55                  60

Gly Ser Pro Tyr Tyr Asp Asn Val Arg Pro Leu Ser Tyr Pro Asp Ser
65                  70                  75                  80

Asp Ala Val Leu Ile Cys Phe Asp Ile Ser Arg Pro Glu Thr Leu Asp
                85                  90                  95

Ser Val Leu Lys Lys Trp Lys Gly Glu Ile Gln Glu Phe Cys Pro Asn
            100                 105                 110

Thr Lys Met Leu Leu Val Gly Cys Lys Ser Asp Leu Arg Thr Asp Val
        115                 120                 125

Ser Thr Leu Val Glu Leu Ser Asn His Arg Gln Thr Pro Val Ser Tyr
    130                 135                 140

Asp Gln Gly Ala Asn Met Ala Lys Gln Ile Gly Ala Ala Thr Tyr Ile
145                 150                 155                 160

Glu Cys Ser Ala Leu Gln Ser Glu Asn Ser Val Arg Asp Ile Phe His
                165                 170                 175

Val Ala Thr Leu Ala Cys Val Asn Lys Thr Asn Lys Asn Val Lys Arg
```

```
                180                 185                 190
Asn Lys Ser Gln Arg Ala Thr Lys Arg Ile Ser His Met Pro Ser Arg
            195                 200                 205

Pro Glu Leu Ser Ala Val Ala Thr Asp Leu Arg Lys Asp Lys Ala Lys
        210                 215                 220

Ser Cys Thr Val Met
225

<210> SEQ ID NO 24
<211> LENGTH: 689
<212> TYPE: DNA
<213> ORGANISM: Artificial Sequence
<220> FEATURE:
<223> OTHER INFORMATION: Synthetic construct

<400> SEQUENCE: 24
atggatccta atcagaacgt gaaatgcaag atagttgtgg tgggagacag tcagtgtgga    60
aaaactgcgc tgctccatgt cttcgccaag gactgcttcc ccgagaatta cgttcctaca   120
gtgtttgaga attacacggc cagttttgaa atcgacacac aaagaataga gttgagcctg   180
tgggacactt cgggttctcc ttactatgac aatgtccgcc ccctctctta ccctgattcg   240
gatgctgtgc tgatttgctt tgacatcagt agaccagaga ccctggacag tgtcctcaaa   300
aagtggaaag gtgaaatcca ggaattttgt ccaaatacca aaatgctctt ggtcggctgc   360
aagtctgatc tgcggacaga tgttagtaca ttagtagagc tctccaatca caggcagacg   420
ccagtgtcct atgaccaggg ggcaaatatg gccaaacaga ttggagcagc tacttatatc   480
gaatgctcag ctttacagtc ggaaaatagc gtcagagaca tttttcacgt tgccaccttg   540
gcatgtgtaa ataagacaaa taaaaacgtt aagcggaaca atcacagag agccacaaag   600 cggatttcac acatgcctag cagaccagaa ctctcggcag ttgctacgga cttacgaaag   660
gacaaagcga gagctgcac tgtgatgtg                                      689

<210> SEQ ID NO 25
<211> LENGTH: 22
<212> TYPE: DNA
<213> ORGANISM: Artificial Sequence
<220> FEATURE:
<223> OTHER INFORMATION: Synthetic construct

<400> SEQUENCE: 25 ggttgcttt gtggcttggg ag                                              22

<210> SEQ ID NO 26
<211> LENGTH: 22
<212> TYPE: DNA
<213> ORGANISM: Artificial Sequence
<220> FEATURE:
<223> OTHER INFORMATION: Synthetic construct

<400> SEQUENCE: 26
gattgacgca ctgccaggag ta                                             22

<210> SEQ ID NO 27
<211> LENGTH: 23
<212> TYPE: DNA
<213> ORGANISM: Artificial Sequence
<220> FEATURE:
<223> OTHER INFORMATION: Synthetic construct

<400> SEQUENCE: 27
```
catcttggag gtctatggtg tcc                                                    23

<210> SEQ ID NO 28
<211> LENGTH: 22
<212> TYPE: DNA
<213> ORGANISM: Artificial Sequence
<220> FEATURE:
<223> OTHER INFORMATION: Synthetic construct

<400> SEQUENCE: 28
gaccgtgtaa ccacctggta ct                                                     22

<210> SEQ ID NO 29
<211> LENGTH: 22
<212> TYPE: DNA
<213> ORGANISM: Artificial Sequence
<220> FEATURE:
<223> OTHER INFORMATION: Synthetic construct

<400> SEQUENCE: 29
acaaccgcaa ctgcctcagt ct                                                     22

<210> SEQ ID NO 30
<211> LENGTH: 22
<212> TYPE: DNA
<213> ORGANISM: Artificial Sequence
<220> FEATURE:
<223> OTHER INFORMATION: Synthetic construct

<400> SEQUENCE: 30
gaatctgcct ccaggttctc ag                                                     22

<210> SEQ ID NO 31
<211> LENGTH: 23
<212> TYPE: DNA
<213> ORGANISM: Artificial Sequence
<220> FEATURE:
<223> OTHER INFORMATION: Synthetic construct

<400> SEQUENCE: 31
gacagccatt gtcaggagaa acc                                                    23

<210> SEQ ID NO 32
<211> LENGTH: 22
<212> TYPE: DNA
<213> ORGANISM: Artificial Sequence
<220> FEATURE:
<223> OTHER INFORMATION: Synthetic construct

<400> SEQUENCE: 32
tgcaggagga tctcatggtg tc                                                     22

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33
atctgcctcc tcccttttta                                                        20

<210> SEQ ID NO 34
<211> LENGTH: 20
<212> TYPE: DNA
<213> ORGANISM: Artificial Sequence

```
<220> FEATURE:
<223> OTHER INFORMATION: Synthetic construct

<400> SEQUENCE: 34
tttgctggat aatttctggc                                                  20

<210> SEQ ID NO 35
<211> LENGTH: 147
<212> TYPE: DNA
<213> ORGANISM: Artificial Sequence
<220> FEATURE:
<223> OTHER INFORMATION: Synthetic construct

<400> SEQUENCE: 35
cacactgact gtctcccacc acaactatct tgcatttcac gttctgatta ggatccatga      60
tagatttgct ggataatttc tggcttgctc ttctctcctt tgatgttgcc ttatttctc      120 ttggaacagg aatttctct taagaag                                           147

<210> SEQ ID NO 36
<211> LENGTH: 147
<212> TYPE: DNA
<213> ORGANISM: Artificial Sequence
<220> FEATURE:
<223> OTHER INFORMATION: Synthetic construct

<400> SEQUENCE: 36
cacactgact gtctcccacc acaactatct tgcatttcac gttctgatta ggatcgatag      60
atttgctgga taatttctgg cttgctcttc tctccttcat tgatgttgcc ttatttctc      120 ttggaacagg aatttctct taagaag                                           147

<210> SEQ ID NO 37
<211> LENGTH: 20
<212> TYPE: DNA
<213> ORGANISM: Artificial Sequence
<220> FEATURE:
<223> OTHER INFORMATION: Synthetic construct

<400> SEQUENCE: 37
gggcggacat tgtcatagta                                                  20
```

METHODS AND COMPOSITIONS RELATED TO RNA-TARGETED RHO SMALL GTPase RND3/RhoE THERAPY

STATEMENT REGARDING FEDERALLY SPONSORED RESEARCH OR DEVELOPMENT

This invention was made with government support under Grant No. R01HL141215, awarded by the National Institutes of Health. The government has certain rights in the invention.

REFERENCE TO AN ELECTRONIC SEQUENCE LISTING

The content of the electronic sequence listing submitted on May 21, 2024 as a text file named "11164-011 US1_2024_05_20_ST25_Corrected Sequence Listing" created on May 20, 2024, and having a size of 13,672 bytes, is hereby incorporated by reference in its entirety pursuant to 37 CFR 1.52(e)(5).

BACKGROUND

The Rho family of GTPases consists of 20 members including RhoE. The Rho proteins belong to the Ras superfamily and these small GTPases function as G signaling proteins that convert and amplify external signals into cellular effects (Boureux 2007; Lawson 2018). Rho GTPases have shown to regulate many aspects of intracellular actin dynamics, such as cytoskeleton rearrangement, cell migration, vesicular trafficking, cell polarity, cell cycle, and transcriptional dynamics (Hodge 2016; Jie 2015; Dai 2018). In mammals, the Rho family contains 20 members (Boureux 2007). Though the majority of them are respectively activated and deactivated by the GTP-bound and GDP-bound cycling, "atypical" GTPases in the Rnd subgroup are unusual as they are constitutively GTP bound (Foster 1996; Guash 1998). Therefore, it is not regulated by GTP/GDP cycling, but by the expression level and by protein modifications, such as prenylation and phosphorylation (Jie 2015). There are three members, Rnd1, Rnd2, and Rnd3/RhoE, in the Rnd subgroup and Rnd3/RhoE is the most extensively studied member. The current paradigm, derived from the majority of the published studies on RhoE, is that RhoE functions as a repressor that directly inhibits the RhoA effector Rho-associated coiled-coil kinase 1 (ROCKt) (Riento & Ridley 2003; Riento & Gausch 2003). While the regulatory roles of RhoE have been almost entirely linked to cell actin cytoskeleton dynamics, cell migration, and apoptosis in its early studies (Riento & Gausch 2003; Ongusaha 2006; Villalonga 2004; Maekawa 1999; Arber 1998). Versatile functions of RhoE in intracellular $Ca^{2+}$ homeostasis regulation (Yang 2015), apoptosis (Yue 2014), angiogenesis (Yue 2016), inflammation (Dai 2019), brain development (Lin 2013), and glioblastoma genesis (Liu 2015; Liu 2016) along with other groups (Azzarelli 2014). All of these studies show a broad spectrum of biological and pathological functions of RhoE.

GTP binding domain of RND3 protein becomes the most often targeted site for RND3 inhibitor drug screening. Almost all of the drug screening approaches currently used center on finding a molecule that specifically binds to this GTP binding domain to inhibit RND3 activity. However, the challenge of this approach is drug targeting specificity. The sequences and structures of GTP binding domain among all GTPase proteins are highly similar. What is needed in the art are molecules that specifically bind to the GTP binding domain of RND3 protein but no other GTPase proteins' GTP binding domain.

SUMMARY

Disclosed herein is an isolated nucleic acid molecule, wherein said molecule comprises 90% or more identity to SEQ ID NO: 1, SEQ ID NO: 2, SEQ ID NO: 3, or SEQ ID NO: 4.

Also disclosed herein is a composition comprising a) an isolated nucleic acid molecule comprising 90% or more identity to SEQ ID NO: 1; and b) an isolated nucleic acid molecule comprising 90% or more identity to SEQ ID NO: 2.

Further disclosed herein is a composition comprising a) an isolated nucleic acid molecule comprising 90% or more identity to SEQ ID NO: 3; and b) an isolated nucleic acid molecule comprising 90% or more identity to SEQ ID NO: 4.

Disclosed herein is a composition comprising: a. an isolated nucleic acid molecule comprising 90% or more identity to SEQ ID NO: 1; b. an isolated nucleic acid molecule comprising 90% or more identity to SEQ ID NO: 2; c.an isolated nucleic acid molecule comprising 90% or more identity to SEQ ID NO: 3; and d. an isolated nucleic acid molecule comprising 90% or more identity to SEQ ID NO: 4.

Also disclosed is an isolated nucleic acid molecule, wherein said molecule comprises 90% or more identity to SEQ ID NO: 5, SEQ ID NO: 6, SEQ ID NO: 7, or SEQ ID NO: 8.

Further disclosed is an isolated nucleic acid molecule, wherein said molecule comprises 90% or more identity to SEQ ID NO: 9, SEQ ID NO: 10, SEQ ID NO: 11, or SEQ ID NO: 12.

Yet further disclosed is an isolated nucleic acid molecule, wherein said molecule comprises 90% or more identity to SEQ ID NO: 13, SEQ ID NO: 14, SEQ ID NO: 15, or SEQ ID NO: 16.

Even further disclosed is an isolated nucleic acid molecule, wherein said molecule comprises 90% or more identity to SEQ ID NO: 17, SEQ ID NO: 18, SEQ ID NO: 19, or SEQ ID NO: 20.

Disclosed is a composition comprising a) an isolated nucleic acid molecule comprising 90% or more identity to SEQ ID NO: 9; and b) an isolated nucleic acid molecule comprising 90% or more identity to SEQ ID NO: 10.

Also disclosed is a composition comprising a) an isolated nucleic acid molecule comprising 90% or more identity to SEQ ID NO: 11; and b) an isolated nucleic acid molecule comprising 90% or more identity to SEQ ID NO: 12.

Further disclosed is a composition comprising: a. an isolated nucleic acid molecule comprising 90% or more identity to SEQ ID NO: 9; b. an isolated nucleic acid molecule comprising 90% or more identity to SEQ ID NO: 10; c. an isolated nucleic acid molecule comprising 90% or more identity to SEQ ID NO: 11; and d. an isolated nucleic acid molecule comprising 90% or more identity to SEQ ID NO: 12.

Also disclosed is an isolated nucleic acid molecule comprising 90% or more identity to a nucleic acid comprising both SEQ ID NO: 13 and SEQ ID NO: 17, wherein SEQ ID NO: 13 and SEQ ID NO: 17 are separated by a linking nucleic acid.

Further discloses is an isolated nucleic acid molecule comprising 90% or more identity to a nucleic acid comprising both SEQ ID NO: 14 and SEQ ID NO: 18, wherein SEQ ID NO: 14 and SEQ ID NO: 18 are separated by a linking nucleic acid.

Disclosed is an isolated nucleic acid molecule comprising 90% or more identity to a nucleic acid comprising both SEQ ID NO: 15 and SEQ ID NO: 19, wherein SEQ ID NO: 15 and SEQ ID NO: 19 are separated by a linking nucleic acid.

Further disclosed is an isolated nucleic acid molecule comprising 90% or more identity to a nucleic acid comprising both SEQ ID NO: 16 and SEQ ID NO: 20, wherein SEQ ID NO: 16 and SEQ ID NO: 20 are separated by a linking nucleic acid.

Disclosed herein is a method of treating a subject with a condition related to functional regulation mediated by RND3 or RhoEα, the method comprising administering to the subject a composition comprising an isolated nucleic acid comprising at least 90% identity to one or more of SEQ ID NOS: 1, 2, 3, or 4.

Also disclosed is a method of treating a subject with a condition related to functional regulation mediated by RND3 or RhoEα, the method comprising administering to the subject a composition comprising an isolated nucleic acid comprising at least 90% identity to one or more of SEQ ID NOS: 5, 6, 7, or 8.

Disclosed is a method of treating a subject with a condition related to functional regulation mediated by RND3 or RhoEα, the method comprising administering to the subject a composition comprising an isolated nucleic acid comprising at least 90% identity to one or more of: a. SEQ ID NO: 13 and SEQ ID NO: 17, wherein SEQ ID NO: 13 and SEQ ID NO: 17 are separated by a linking nucleic acid; b. SEQ ID NO: 14 and SEQ ID NO: 18, wherein SEQ ID NO: 14 and SEQ ID NO: 18 are separated by a linking nucleic acid; c. SEQ ID NO: 15 and SEQ ID NO: 19, wherein SEQ ID NO: 15 and SEQ ID NO: 19 are separated by a linking nucleic acid; or d. SEQ ID NO: 16 and SEQ ID NO: 20, wherein SEQ ID NO: 16 and SEQ ID NO: 20 are separated by a linking nucleic acid Disclosed herein is a method of detecting a modulator specific for an N-terminal region of RND3, the method comprising: a. providing an isolated RND3 protein or a fragment thereof, wherein said fragment comprises 90% or more identity to amino acids 1-15 of SEQ ID NO: 21; b. exposing the RND3 protein to a test potential modulator; and c. detecting interaction between the test potential modulator and the N-terminal region of RND3, wherein the test potential modulator interacts at the region with 90% or more identity to amino acids 1-15 of SEQ ID NO: 21, thereby detecting a potential modulator specific for the N-terminal region of RND3.

Also disclosed is a method of detecting a potential nucleic acid inhibitor of RND3 expression, wherein said potential nucleic acid inhibitor is specific for the region encoding the N-terminal of RND3, the method comprising: a. providing an isolated nucleic acid encoding RND3 or a fragment thereof, wherein said fragment comprises 90% or more identity to nucleotides 1-45 of SEQ ID NO: 23; b. exposing the isolated nucleic acid of step a) to a test potential nucleic acid inhibitor; and c. detecting interaction between the test potential nucleic acid inhibitor and the nucleic acid encoding RND3 or a fragment thereof, wherein the test potential nucleic acid inhibitor is determined to interact at the region with 90% or more identity to nucleotides 1-45 of SEQ ID NO: 23, thereby detecting a potential nucleic acid inhibitor of the N-terminal region of RND3 expression, wherein said potential nucleic acid inhibitor is specific for the region encoding the N-terminal of RND3.

DETAILED DESCRIPTION

General Definitions

Figure 1:
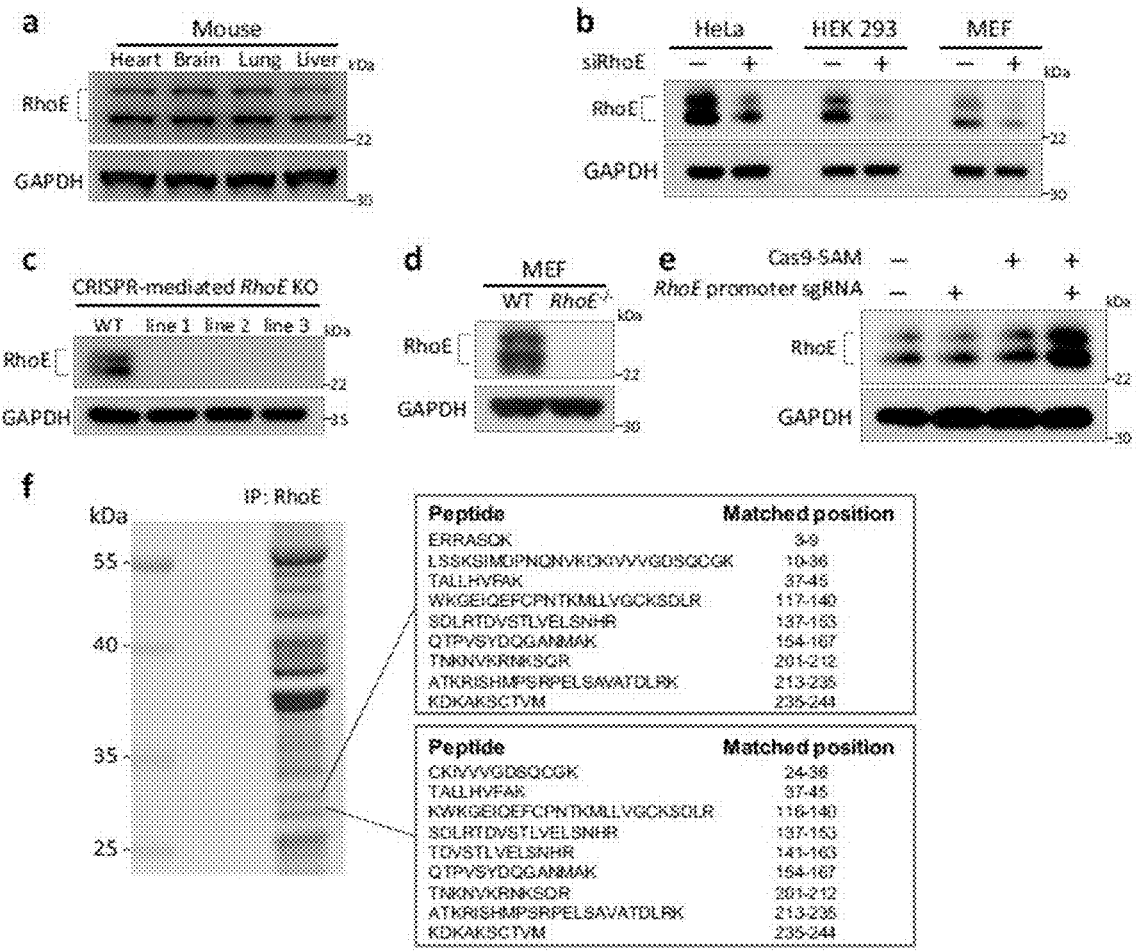
FIG. 1A-F shows A) Immunoblot for RhoE in wild-type mouse tissues. B) Expression of RhoE in normal and RhoE knockdown cell lines. Indicated cells were transfected with either nontargeting siRNA or RhoE-specific siRNA. C) Immunoblot for RhoE in wild-type and CRISPR-mediated RhoE knockout (RhoE KO) HeLa cells. Three RhoE KO cell clones were presented. D) Immunoblot for RhoE in MEF cells from wild-type and RhoE null (RhoE−/−) mice. E) Transcriptional activation of RhoE in HeLa cells by Cas9-synergistic activation mediator (SAM). RhoE promoter-specific sgRNA was transfected along with the Cas9-SAM components in HeLa cells. Cell lysates were immunoblotted for RhoE. F) Protein pull-down using RhoE antibody in HEK 293 cells, followed by LC-MS/MS assay. Peptides identified from the upper and lower gel band were aligned to RhoE protein sequence.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "pharmaceutically acceptable" component can refer to a component that is not biologically or otherwise undesirable, i.e., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Vector" used herein means, in respect to a nucleic acid sequence, a nucleic acid sequence comprising a regulatory nucleic acid sequence that controls the replication of an expressible gene. A vector may be either a self-replicating, extrachromosomal vector or a vector which integrates into a host genome. Alternatively, a vector may also be a vehicle comprising the aforementioned nucleic acid sequence. A vector may be a plasmid, bacteriophage, viral particle (isolated, attenuated, recombinant, etc.). A vector may comprise a double-stranded or single-stranded DNA, RNA, or hybrid DNA/RNA sequence comprising double-stranded and/or single-stranded nucleotides. In some embodiments, the vector is a viral vector that comprises a nucleic acid sequence that is a viral packaging sequence responsible for packaging one or a plurality of nucleic acid sequences that encode one or a plurality of polypeptides. In some embodiments, the vector is a plasmid. In some embodiments, the vector is a viral particle. In some embodiments, the vector is viral vector with a natural and/or an engineered capsid. In some embodiments, the viral vector is a lentiviral vector.

Viral vector systems which can be utilized with the methods and compositions described herein include, but are not limited to, (a) adenovirus vectors; (b) retrovirus vectors, including but not limited to lentiviral vectors, Moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an RNA will generally require regulatory elements, e.g., promoters, enhancers, etc., to ensure the expression of the desired molecule a functional fragment thereof in target cells. Other aspects to consider for vectors and constructs are further described below.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

RND3, referred to alternately as RhoE (SEQ ID NO: 21), is a small GTPase protein. The GTP binding domain of RND3 protein is the most often targeted site for RND3 inhibitor drug screening. Almost all of the drug screening approaches that have used up until now attempt to find a molecule that specifically binds to this GTP binding domain to inhibit RND3 activity. However, the challenge of this approach is drug targeting specificity. The sequences and structures of the GTP binding domain among all GTPase proteins are highly similar. It is extremely difficult to identify a molecule that specifically binds to the GTP binding domain of RND3 protein but no other GTPase proteins' GTP binding domain. siRNA-induced RND3 inhibition avoids this challenge by directly and specifically targeting RND3 mRNA but not protein.

Furthermore, a short isoform of RND3 named as RhoEα was discovered (SEQ ID NO: 23). It is 45-nucleotides shorter compared to the full length RND3 molecule at the N-terminus. Sequence alignment analysis shows that the 45-nucleotide region is unique for RND3. Other RND gene family members, including RND1 and RND2, do not contain this region. This led to the design of siRNA oligos targeting this unique region to achieve the best specificity for RND3 in RNA-mediated drug targeting, which are disclosed herein.

Compositions and methods comprising siRNA targeted to RhoE mRNA are advantageously used in the functional regulation of Rnd3. The basic role of RND3 is to report as an endogenous antagonist of RhoA signaling-mediated actin cytoskeleton dynamics, which specifically contributes to cell migration and neuron polarity. In addition, RND3 also plays a critical role in arresting cell cycle distribution, inhibiting cell growth, and inducing apoptosis and differentiation. Increasing data have shown that aberrant RND3 expression may be the leading cause of some systemic diseases; particularly highlighted in apoptotic cardiomyopathy, developmental arrhythmogenesis and heart failure, hydrocephalus, as well as tumor metastasis and chemotherapy resistance (Jie 2015).

The siRNAs of the invention cause the RNAi-mediated degradation of RhoE mRNA, so that the protein product of the RhoE gene is not produced or is produced in reduced amounts. Because the RhoE gene product is required for certain intercellular events, the siRNA-mediated degradation of RhoE mRNA inhibits these functions.

The invention therefore provides isolated siRNA comprising short double-stranded RNA from about 17 nucleotides to about 29 nucleotides in length, preferably from about 19 to about 25 nucleotides in length, that are targeted to the target mRNA. The siRNA comprise a sense RNA strand and a complementary antisense RNA strand annealed together by standard Watson-Crick base-pairing interactions (hereinafter "base-paired"). As is described in more detail below, the sense strand comprises a nucleic acid sequence which is substantially identical to a target sequence contained within the target mRNA.

In one embodiment of the invention, the antisense strand of the siRNA has at least near-perfect contiguous complementarity of at least 19 nucleotides with the target mRNA. "Near-perfect," as used herein, means the antisense strand of the siRNA is "substantially complementary to," and the sense strand of the siRNA is "substantially identical to" at least a portion of the target mRNA. "Identity," as known by one of ordinary skill in the art, is the degree of sequence relatedness between nucleotide sequences as determined by matching the order and identity of nucleotides between the sequences. In one embodiment, the antisense strand of an siRNA having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) J. Mol. Biol. 215:403-410).

The term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

The relationship between a target mRNA (sense strand) and one strand of an siRNA (the sense strand) is that of identity. The sense strand of an siRNA is also called a passenger strand, if present. The relationship between a target mRNA (sense strand) and the other strand of an siRNA (the antisense strand) is that of complementarity. The antisense strand of an siRNA is also called a guide strand.

The penultimate base in a nucleic acid sequence that is written in a 5' to 3' direction is the next to the last base, i.e., the base next to the 3' base. The penultimate 13 bases of a nucleic acid sequence written in a 5' to 3' direction are the last 13 bases of a sequence next to the 3' base and not including the 3' base. Similarly, the penultimate 14, 15, 16, 17, or 18 bases of a nucleic acid sequence written in a 5' to 3' direction are the last 14, 15, 16, 17, or 18 bases of a sequence, respectively, next to the 3' base and not including the 3' base.

The phrase "a region of at least 13 contiguous nucleotides having at least 90% sequence complementarity to, or at least 90% sequence identity with, the penultimate 13 nucleotides of the 3' end of an mRNA corresponding to any one of (a sequence identifier)" allows a one nucleotide substitution. Two nucleotide substitutions (i.e., 11/13=85% identity/complementarity) are not included in such a phrase.

In one embodiment of the invention, the region of contiguous nucleotides is a region of at least 14 contiguous nucleotides having at least 85% sequence complementarity to, or at least 85% sequence identity with, the penultimate 14 nucleotides of the 3' end of an mRNA corresponding to the sequence identified by each sequence identifier. Two nucleotide substitutions (i.e., 12/14=86% identity/complementarity) are included in such a phrase.

In a further embodiment of the invention, the region of contiguous nucleotides is a region of at least 15, 16, 17, or 18 contiguous nucleotides having at least 80% sequence complementarity to, or at least 80% sequence identity with, the penultimate 14 nucleotides of the 3' end of an mRNA corresponding to the sequence of the sequence identifier. Three nucleotide substitutions are included in such a phrase.

Specifically, disclosed herein is a first set of oligonucleotide that can be used as siRNA molecules. The first set, which is specific for the N-terminal region of RhoE (RND3) is represented by SEQ ID NOS: 1 and 2, which represent the sense and antisense strands. The second set, which targets the C-terminal region of RhoE (RND3) is represented by SEQ ID NOS: 3 and 4, which represent the sense and antisense strands. These siRNA molecules can be used individually, or in pairs (such as SEQ ID NOS: 1 and 2, and SEQ ID NOS: 3 and 4), or all four can be used together (SEQ ID NOS: 1-4 in the same composition). Therefore, disclosed herein are compositions comprising individual siRNAs, pairs of siRNAs, or multiple pairs of siRNAs.

Also disclosed herein are shRNA (small hairpin RNA) molecules. shRNA are sequences of RNA, typically about 80 base pairs in length, that include a region of internal hybridization that creates a hairpin structure. shRNA molecules are processed within the cell to form siRNA which in turn knock down gene expression. The benefit of shRNA is that they can be incorporated into plasmid vectors and integrated into genomic DNA for longer-term or stable expression, and thus longer knockdown of the target mRNA. Examples of vectors which can be used with the shRNAs are given below.

As used herein, a nucleic acid sequence "substantially identical" to a target sequence contained within the target mRNA is a nucleic acid sequence which is identical to the target sequence, or which differs from the target sequence by one or more nucleotides. Sense strands of the invention which comprise nucleic acid sequences substantially identical to a target sequence are characterized in that siRNA comprising such sense strands induce RNAi-mediated degradation of mRNA containing the target sequence. For example, an siRNA of the invention can comprise a sense strand comprise nucleic acid sequences which differ from a target sequence by one, two or three or more nucleotides, as long as RNAi-mediated degradation of the target mRNA is induced by the siRNA.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, Molecular Cloning: A Laboratory Manual, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature (Tm) of the hybrid where Tm is determined for hybrids between 19 and 49 base pairs in length using the following calculation: Tm° C.=81.5+16.6(log 10 [Na+])+ 0.41 (% G+C)−(600/N) where N is the number of bases in the hybrid, and [Na+] is the concentration of sodium ions in the hybridization buffer.

The sense and antisense strands of the present siRNA can comprise two complementary, single-stranded RNA molecules or can comprise a single molecule in which two complementary portions are base-paired and are covalently linked by a single-stranded "hairpin" area. As discussed above, this is referred to herein as a short hairpin RNA (shRNA). Without wishing to be bound by any theory, it is believed that the hairpin area of the latter type of siRNA molecule is cleaved intracellularly by the "Dicer" protein (or its equivalent) to form a siRNA of two individual base-paired RNA molecules.

Examples of cDNAs encoding shRNA molecules can be found in SEQ ID NOS: 5 and 6, which correspond to siRNAs SEQ ID NOS: 1 and 2. Also disclosed is the shRNA set SEQ ID NOS: 7 and 8, which correspond to siRNAs SEQ ID NOS: 3 and 4. These shRNAs can be presented as individual pairs in a composition, such as SEQ ID NOS: 5 and 6 together, and SEQ ID NOS: 7 and 8 together, or all four shRNAs can be used in the same composition.

The hairpins of the shRNAs disclosed herein can be made of any nucleic acid which is capable of forming a hairpin. One of skill in the art will understand how to design hairpins for shRNA. Therefore, SEQ ID NOS: 9-12 correspond to SEQ ID NOS: 5-8, but are comprised of generic sequences, which represent any hairpin of 7 nucleotides in length. These generic sequences that represent the hairpin are referred to in these sequences by multiple "X's", which means that position in the nucleic acid can be any nucleotide. It is also important to note that the hairpin can be any length. For example, the hairpin can be 2, 3, 4, 5, 6, 7, 8, 9, 10, 11, 12, 13, 14, 15, or more nucleotides in length. One of skill in the art can design hairpins of an appropriate length to form a functional shRNA.

One of skill in the art will appreciate that any of SEQ ID NOS: 13-16, which represent the first part of the shRNA molecules found in SEQ ID NOS: 9-12, can be covalently attached to a nucleic acid linker, which can later form a hairpin, at its 5' or 3' end, which is then covalently linked to the 5' or 3' end of any one of SEQ ID NOS: 17-20, which represent the second part of the shRNA molecules found in SEQ ID NOS: 9-12, respectively. The linker, which joins the first and second nucleic acids which are complementary to each other, can form a hairpin upon the hybridization of the nucleic molecules which it links. For example, the 3' end of SEQ ID NO: 13 can be attached to a linker at the 5' end of the linker, and the 3' end of the linker can be attached to the 5' end of SEQ ID NO: 17. Because SEQ ID NO 13 and SEQ ID NO: 17 are reverse complements of each other, they can hybridize, leaving the linker to form a hairpin. An example of such as molecule can be found in SEQ ID NO: 9. To illustrate, a cDNA molecule representing an shRNA can be designed such as this: SEQ ID NO: 13—hairpin—SEQ ID NO: 17, wherein SEQ ID NOS: 13 and 17 are reverse complements of each other.

The shRNA molecules can be combined into a composition, so that SEQ ID NOS: 5 and 6 can be in the same composition, SEQ ID NOS: 7 and 8 can be in the same composition, or all of SEQ ID NOS: 5-8 can be in the same composition. This is also true for SEQ ID NOS: 9-12, which can be in a composition singly, in pairs (SEQ ID NOS: 9 and 10, and SEQ ID NOS: 11 and 12), or in a composition with all four molecules. This is also true for SEQ ID NOS: 13-16, and for SEQ ID NOS: 17-20, which represent generic sequences which can be combined together in any fashion desired.

As used herein, "isolated" means synthetic, or altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered. By way of example, siRNA which are produced inside a cell by natural processes, but which are produced from an "isolated" precursor molecule, are "isolated" molecules. Thus, an isolated dsRNA or protein can be introduced into a target cell, where it is processed by the Dicer protein (or its equivalent) into isolated siRNA.

As used herein, "target mRNA" means human RhoE mRNA, mutant or alternative splice forms of human RhoE mRNA, or mRNA from cognate RhoE genes, or isoforms thereof, such as RhoEα. The human RhoE mRNA sequence is given in SEQ ID NO: 22 as the cDNA equivalent. One skilled in the art would understand that the cDNA sequence is equivalent to the mRNA sequence, and can be used for the same purpose herein; i.e., the generation of siRNA for inhibiting expression of RhoE or the isoform RhoEα.

Figure 3:
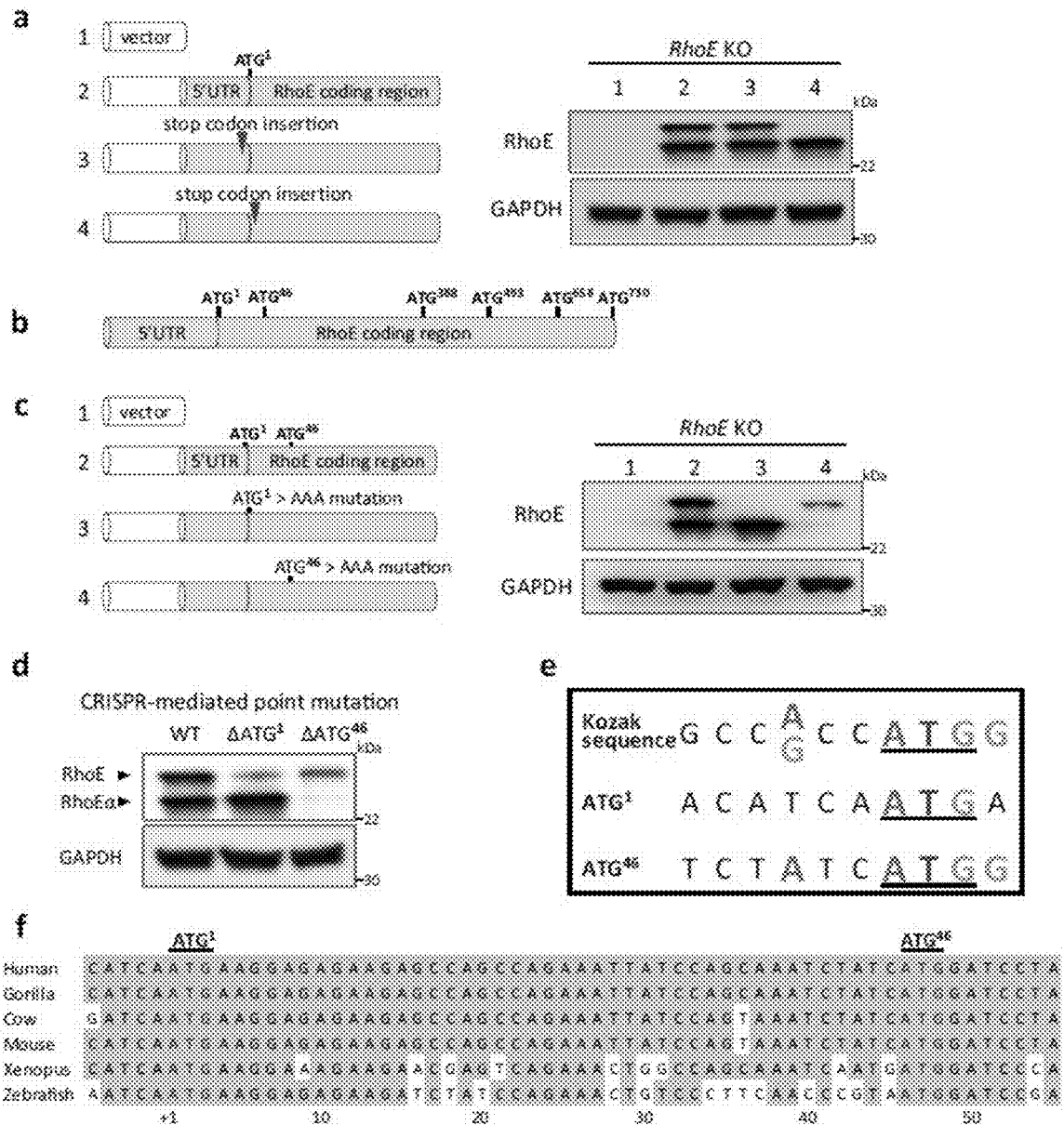
FIG. 3A-F shows A) RhoE expression vector was mutated by the stop codon insertion before and after ATG1. RhoE knockout HeLa cells were transfected with indicated plasmids and cell lysates were immunoblotted. B) Schematic of potential alternative translation start sites in RhoE coding region. C) ATG1 and ATG46 were individually mutated to AAA. RhoE knockout HeLa cells were transfected with indicated plasmids and cell lysates were immunoblotted. D) Single-stranded donor oligonucleotides (ssODN) were designed for inducing either ATG1 or ATG46 genomic deletion. HeLa cells were co-transfected with the Cas9; RhoE sgRNA plasmid and the indicated ssODN. Cell lysates were immunoblotted. E) Comparison of Kozak sequences around human RhoE translation initiation sites. The strongest Kozak context promoting translation initiation contains a purine, preferably adenine A, 3 bp before ATG, and a guanine G following ATG. F) Conservation analysis for RhoEα translation start site among species. Human is SEQ ID NO: 37, gorilla is also SEQ ID NO: 37, Cow is SEQ ID NO: 38, Mouse is SEQ ID NO: 39, *Xenopus* is SEQ ID NO: 40, and Zebrafish is SEQ ID NO: 41.

As used herein, a gene or mRNA which is "cognate" to human RhoE is a gene or mRNA from another mammalian species which is homologous to human RhoE. For example, the cognate RhoE mRNA from other animals is shown in FIG. 3F.

Other siRNAs than those given herein can be designed to be specific for RhoE. The mRNA transcribed from the human RhoE gene can be analyzed for alternative splice forms using techniques well-known in the art. Such techniques include reverse transcription-polymerase chain reaction (RT-PCR), northern blotting and in-situ hybridization. Techniques for analyzing mRNA sequences are described, for example, in Busting S A (2000), J. Mol. Endocrinol. 25: 169-193, the entire disclosure of which is herein incorporated by reference. Representative techniques for identifying alternatively spliced mRNAs are also described below.

For example, databases that contain nucleotide sequences related to a given disease gene can be used to identify alternatively spliced mRNA. Such databases include GenBank, Embase, and the Cancer Genome Anatomy Project (CGAP) database. The CGAP database, for example, contains expressed sequence tags (ESTs) from various types of human cancers. An mRNA or gene sequence from the RhoE gene can be used to query such a database to determine whether ESTs representing alternatively spliced mRNAs have been found.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e.g., the use of 2'-substituted ribonucleotides or modifications to the sugar-phosphate backbone); or the substitution of one or more nucleotides in the siRNA with deoxyribonucleotides. siRNA which are exposed to serum, lachrymal fluid or other nuclease-rich environments, or which are delivered topically (e.g., by eyedropper), are preferably altered to increase their resistance to nuclease degradation.

One or both strands of the siRNA of the invention can also comprise a 3' overhang. As used herein, a "3' overhang" refers to at least one unpaired nucleotide extending from the 3'-end of an RNA strand. Such an overhang can be found in SEQ ID NOS: 1-4. One of skill in the art will appreciate that overhangs can be designed to promote maximum efficiency of the siRNAs.

Thus in one embodiment, the siRNA of the invention comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length.

In order to enhance the stability of the present siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

The siRNA of the invention can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Göttingen, Germany, and can be found by accessing the website of the Max Planck Institute and searching with the keyword "siRNA." Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nucleotides downstream (i.e., in the 3' direction) from the start codon. The target sequence can, however, be located in the 5' or 3' untranslated regions, or in the region nearby the start codon.

The siRNA of the invention can be obtained using a number of techniques known to those of skill in the art. For example, the siRNA can be chemically synthesized or recombinantly produced using methods known in the art, such as the *Drosophila* in vitro system described in U.S. published application 2002/0086356 of Tuschl et al., the entire disclosure of which is herein incorporated by reference.

Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA of the invention from a plasmid include, for example, the U6 or Hi RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA of the invention to cells in vivo is discussed in more detail below.

siRNA of the invention can be expressed from a recombinant plasmid either as two separate, complementary RNA molecules, or as a single RNA molecule with two complementary regions.

Selection of plasmids suitable for expressing siRNA of the invention, methods for inserting nucleic acid sequences for expressing the siRNA into the plasmid, and methods of delivering the recombinant plasmid to the cells of interest are within the skill in the art. See, for example Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat.

Biotechnol. 20: 505-508, the entire disclosures of which are herein incorporated by reference.

The siRNA of the invention can also be expressed from recombinant viral vectors intracellularly in vivo. The recombinant viral vectors of the invention comprise sequences encoding the siRNA of the invention and any suitable promoter for expressing the siRNA sequences. The recombinant viral vectors of the invention can also comprise inducible or regulatable promoters for expression of the siRNA in a particular tissue or in a particular intracellular environment. The use of recombinant viral vectors to deliver siRNA of the invention to cells in vivo is discussed in more detail below.

siRNA of the invention can be expressed from a recombinant viral vector either as two separate, complementary RNA molecules, or as a single RNA molecule with two complementary regions, such as those given in SEQ ID NOS: 5-16.

Any viral vector capable of accepting the coding sequences for the siRNA molecule(s) to be expressed can be used, for example vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; MillerA D (1990), Hum Gene Therap. 1: 5-14; and Anderson W F (1998), Nature 392: 25-30, the entire disclosures of which are herein incorporated by reference.

The ability of an siRNA containing a given target sequence to cause RNAi-mediated degradation of the target mRNA can be evaluated using standard techniques for measuring the levels of RNA or protein in cells. For example, siRNA of the invention can be delivered to cultured cells, and the levels of target mRNA can be measured by Northern blot or dot blotting techniques, or by quantitative RT-PCR. Alternatively, the levels of RND3 protein in the cultured cells can be measured by ELISA or Western blot.

As discussed above, the siRNA of the invention target and cause the RNAi-mediated degradation of human RND3 mRNA, or alternative splice forms, mutants or cognates thereof. Degradation of the target mRNA by the present siRNA reduces the production of a functional gene product from the RhoE gene. Thus, the invention provides a method of inhibiting expression of RND3 in a subject, comprising administering an effective amount of an siRNA of the invention to the subject, such that the target mRNA is degraded.

As the products of the RhoE gene are required cell migration and neuron polarity, cell cycle distribution, inhibition of cell growth, and induction of apoptosis and differentiation, the invention also provides a method of inhibiting these processes by RNAi-mediated degradation of the target mRNA by the present siRNA. In another embodiment, the invention provides a method of treating a subject for complications arising from these conditions.

Methods

Disclosed herein is a method of treating a subject with a condition related to functional regulation mediated by RhoE or RhoEα, the method comprising administering to the subject a composition comprising an isolated nucleic acid comprising at least 90% identity to one or more of the siRNA or shRNA molecules disclosed herein, so one or more of SEQ ID NOS: 1-16. For example, the subject can be treated with SEQ ID NOS: 1 and 2, or SEQ ID NOS: 3 and 4, or all four siRNAs. The subject can also be treated with shRNA, such as those represented by the cDNA equivalent in SEQ ID NOS: 9-12. For example, the subject can be given SEQ ID NOS: 9 and 10, or SEQ ID NOS: 11 and 12, or all four combined. This is also true for SEQ ID NOS: 13-16, which represent SEQ ID NOS: 9-12, but with a generic sequence for the hairpin region. As discussed above, the shRNA can be given in the form of a vector.

Therefore, the methods of treatment disclosed herein incorporate giving a nucleic acid with 80%, 85%, 90%, 95%, or more identity to any one of SEQ ID NOS: 1-4, or 5-8, or 9-12, or any combination of those. The method of treatment can also comprise giving any of SEQ ID NOS: 13-20, alone or in combination, or with other sequences such as linkers that are capable of forming hairpins between them, to a subject in need thereof.

As discussed above, the RNAi molecules disclosed herein can be given for any condition related to RND3 activity. For example, abnormal cell proliferation or differentiation, such as that associated with cancer, such as leukemia, prostate cancer, ovarian cancer, pancreas cancer, lung cancer, breast cancer, liver cancer, head and neck cancer, colon cancer, gastrointestinal cancers, bladder cancer, non-Hodgkin's lymphoma cancer and melanoma. The condition can also be inflammation or calcium homeostasis.

RNAi-mediated degradation of the target mRNA can be detected by measuring levels of the target mRNA or protein in the cells of a subject, using standard techniques for isolating and quantifying mRNA or protein as described above.

Inhibition of RND3-related pathologies can also be evaluated by measuring the progression of the pathology in the subject, for example by detecting actin cytoskeletal rearrangement; regulating cell morphology, cell migration, neuron polarity, and smooth muscle cell contraction; inhibition of cell proliferation; and mediation of cell apoptosis and survival.

Preferably, an siRNA of the invention is used to inhibit the growth or metastasis of solid tumors associated with cancers; for example breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma; skin cancer (e.g., melanoma), lymphomas and blood cancer.

The siRNAs of the invention can be administered to a subject in combination with a pharmaceutical agent which is different from the presently disclosed siRNAs. Alternatively, the siRNA of the invention can be administered to a subject in combination with another therapeutic method designed to treat the pathology. For example, the siRNA of the invention can be administered in combination with therapeutic methods currently employed for treating cancer or preventing tumor metastasis (e.g., radiation therapy, chemotherapy, and surgery). For treating tumors, the siRNA of the invention is preferably administered to a subject in combination with radiation therapy, or in combination with chemotherapeutic agents such as cisplatin, carboplatin, cyclophosphamide, 5-fluorouracil, adriamycin, daunorubicin or tamoxifen. The compositions disclosed herein can also include an adjuvant.

One skilled in the art can readily determine an effective amount of the siRNA of the invention to be administered to a given subject, by taking into account factors such as the size and weight of the subject; the extent of disease penetration; the age, health and sex of the subject; the route of administration; and whether the administration is regional or systemic. Generally, an effective amount of the siRNA of the invention comprises an intercellular concentration at the site where intercellular or cell-matrix adhesion is to be inhibited of from about 1 nanomolar (nM) to about 100 nM, preferably from about 2 nM to about 50 nM, more preferably from about 2.5 nM to about 10 nM. It is contemplated that greater or lesser amounts of siRNA can be administered.

In the present methods, the present siRNA can be administered to the subject either as naked siRNA, in conjunction with a delivery reagent, or as a recombinant plasmid or viral vector which expresses the siRNA.

Suitable delivery reagents for administration in conjunction with the present siRNA include the Mirus Transit TKO lipophilic reagent; lipofectin; lipofectamine; cellfectin; or polycations (e.g., polylysine), or liposomes. A preferred delivery reagent is a liposome.

Liposomes can aid in the delivery of the siRNA to a particular tissue, such as retinal or tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), Ann. Rev. Biophys. Bioeng. 9: 467; and U.S. Pat. Nos. 4,235,871, 4,501,728, 4,837,028, and 5,019,369, the entire disclosures of which are herein incorporated by reference.

Preferably, liposomes encapsulating the present siRNA comprise a ligand molecule that can target the liposome to cells expressing RND3 at or near the site of angiogenesis or other physiological process involving RND3-mediated cell adhesion, such as a tumor. Cells which express RND3 include endothelial, epithelial, fibroblastic, hematopoietic and tumor cells. Ligands which bind to receptors prevalent in tumor or endothelial cells, such as monoclonal antibodies that bind to tumor antigens or endothelial cell surface antigens, are preferred.

Particularly preferably, the liposomes encapsulating the present siRNA are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), P.N.A.S., USA, 18: 6949-53. In addition, the reduced uptake by the RES lowers the toxicity of stealth liposomes by preventing significant accumulation in the liver and spleen. Thus, liposomes of the invention that are modified with opsonization-inhibition moieties are particularly suited to deliver the present siRNA to tumor cells.

Opsonization inhibiting moieties suitable for modifying liposomes are preferably water-soluble polymers with a number average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can include a block copolymer of PEG and either a polyamino acid, polysaccharide, polyamidoamine, polyethyleneamine, or polynucleotide. The opsonization inhibiting polymers can also include natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)

BH3 and a solvent mixture such as tetrahydrofuran and water in a 30:12 ratio at 60° C.

Recombinant plasmids which express siRNA of the invention are discussed above. Such recombinant plasmids can also be administered directly or in conjunction with a suitable delivery reagent, including the Mints Transit LT1 lipophilic reagent; lipofectin; lipofectamine; cellfectin; polycations (e.g., polylysine) or liposomes. Recombinant viral vectors which express siRNA of the invention are also discussed above, and methods for delivering such vectors to cells of a subject which are expressing ICAM-1 are within the skill in the art.

The siRNA of the invention can be administered to the subject by any means suitable for delivering the siRNA to cells which express RND3. Suitable techniques for delivering the siRNA of the invention to RND3-expressing cells include administration of the siRNA to a subject by gene gun, electroporation, nanoparticles, micro-encapsulation, and the like, or by parenteral and enteral administration routes. Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); or direct (e.g., topical) application to the area.

The siRNA of the invention can be administered in a single dose or in multiple doses. Where the administration of the siRNA of the invention is by infusion, the infusion can be a single sustained dose or can be delivered by multiple infusions. Injection of the siRNA directly into the tissue is at or near the site of need is preferred. Multiple injections of the siRNA into the tissue at or near the site of is particularly preferred.

One skilled in the art can also readily determine an appropriate dosage regimen for administering the siRNA of the invention to a given subject. For example, the siRNA can be administered to the subject once, such as by a single injection or deposition at or near the site where it is needed. Alternatively, the siRNA can be administered to a subject multiple times daily or weekly. For example, the siRNA can be administered to a subject once weekly for a period of from about three to about twenty-eight weeks, more preferably from about seven to about ten weeks. It is understood that periodic administrations of the siRNA of the invention for an indefinite length of time may be necessary for subjects suffering from a chronic condition.

Where a dosage regimen comprises multiple administrations, it is understood that the effective amount of siRNA administered to the subject can comprise the total amount of siRNA administered over the entire dosage regimen.

The siRNA of the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

The present pharmaceutical formulations comprise an siRNA of the invention (e.g., 0.1 to 90% by weight), or a physiologically acceptable salt thereof, mixed with a physiologically acceptable carrier medium. Preferred physiologically acceptable carrier media are water, buffered water, saline solutions (e.g., normal saline or balanced saline solutions such as Hank's or Earle's balanced salt solutions), 0.4% saline, 0.3% glycine, hyaluronic acid and the like. Also disclosed herein are adjuvants.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA of the invention. A pharmaceutical composition for aerosol (inhalational) administration can comprise 0.01-20% by weight, preferably 1%-10% by weight, of one or more siRNA of the invention encapsulated in a liposome as described above, and propellant. A carrier can also be included as desired; e.g., lecithin for intranasal delivery.

Methods of Detecting Modulators of RND3

Disclosed herein are methods of detecting a modulator specific for an N-terminal region of RND3, the method comprising: providing an isolated RND3 protein or a fragment thereof, wherein said fragment comprises 90% or more identity to amino acids 1-15 of SEQ ID NO: 21; exposing the RND3 protein to a test potential modulator; and detecting interaction between the test potential modulator and the N-terminal region of RND3, wherein the test potential modulator interacts at the region with 90% or more identity to amino acids 1-15 of SEQ ID NO: 21, thereby detecting a potential modulator specific for the N-terminal region of RND3. In one embodiment, the potential modulator is confirmed as a modulator by detecting activity of RND3 in the presence of the potential modulator as compared to a control.

By "modulate" is meant to alter, by increase or decrease. As used herein, a "modulator" can mean a composition that can either increase or decrease the expression level or activity level of a gene or gene product such as a peptide. Modulation in expression or activity does not have to be complete. For example, expression or activity can be modulated by about 10%, 20%, 30%, 40%, 50%, 60%, 70%, 80%, 90%, 95%, 99%, 100% or any percentage in between as compared to a control cell wherein the expression or activity of a gene or gene product has not been modulated by a composition. The modulator can be an enhancer or inhibitor.

An assay using the system described herein can take place in a cell, or may take place in a cell-free assay. Described herein is such an assay, which makes use of the system described above. One of skill in the art will appreciate that such an assay, such as a small molecule identification assay, can take place in a high-throughput screen, for example. Examples of high throughput screens using a cell-based assay are known to those of skill in the art. The potential modulator can be a small molecule.

Also disclosed herein is a method of detecting a potential nucleic acid inhibitor of RND3 expression, wherein said potential nucleic acid inhibitor is specific for the region encoding the N-terminal of RND3, the method comprising: providing an isolated nucleic acid encoding RND3 or a fragment thereof, wherein said fragment comprises 90% or more identity to nucleotides 1-45 of SEQ ID NO: 23; exposing the isolated nucleic acid of step a) to a test potential nucleic acid inhibitor; and detecting interaction between the test potential nucleic acid inhibitor and the nucleic acid encoding RND3 or a fragment thereof, wherein the test potential nucleic acid inhibitor is determined to interact at the region with 90% or more identity to nucleotides 1-45 of SEQ ID NO: 23, thereby detecting a potential nucleic acid inhibitor of the N-terminal region of RND3 expression, wherein said potential nucleic acid inhibitor is specific for the region encoding the N-terminal of RND3. In one embodiment, the potential nucleic acid inhibitor can be confirmed as a nucleic acid inhibitor by detecting inhibition of expression of RND3 in the presence of the potential nucleic acid inhibitor as compared to a control. The nucleic acid inhibitor can be an interfering nucleic acid, such as an siRNA.

By way of non-limiting illustration, examples of certain embodiments of the present disclosure are given below.

EXAMPLES

Example 1: Identification and Characterization of a New Isoform of GTPase RhoE

Disclosed herein is a short isoform of RhoE designated as RhoEα, the first Rho GTPase isoform generated from alternative translation. Translation of this new isoform is initiated from an alternative start site downstream of and in-frame with the coding region of the canonical RhoE. RhoEα exhibits a similar subcellular distribution while its protein stability is higher than RhoE. RhoEα contains binding capability to RhoE effectors ROCK1, p190RhoGAP and Syx. The distinct transcriptomes of cells with the expression of RhoE and RhoEα, respectively, are demonstrated herein. There are distinctive and overlapping biological functions of RhoEα compared to RhoE. The discovery of RhoEα provides a new scope of understanding the versatile functions of small GTPases and underlines the complexity and diverse roles of small GTPases Results Two protein bands were detected by anti-RhoE antibody. During the studies of biological functions of atypical small GTPase RhoE, two immunoblot bands for RhoE were detected in animal tissues and various cell lines (Dai 2019). FIG. 1a shows a representative immunoblot of RhoE protein expression in mouse heart, brain, lung, and liver. The two immunoblot protein bands were detected in HeLa, HEK293, and mouse embryonic fibroblast (MEF) cells as well (FIG. 1b), and their expression levels can be decreased by the treatment of siRNA specific for RhoE in these cells (FIG. 1b). Three HeLa cell lines of RhoE knockout were generated by CRISPR, and a complete elimination of the two immunoblot bands was detected in all three cell lines (FIG. 1c). To validate the knockout result in vivo, RhoE expression was assessed in RhoE null MEF cells isolated from RhoE global knockout mice (Yang 2015), and it was found that genetic silencing of RhoE completely removed the two immunoblot bands (FIG. 1d), suggesting that both protein bands are highly associated with RhoE.

To determine if the expression of two RhoE immunoblot bands shared the same transcription promoter, Cas9-synergistic activation mediator (Cas9-SAM) was introduced along with the sgRNA specifically targeting RhoE promoter. The result showed a dramatic increase in both immunoblot bands when RhoE promoter was transcriptionally activated (FIG. 1e), indicating that the two immunoblots of RhoE were transcriptionally regulated by the same promoter and were both originated from the RhoE gene.

Figure 2:
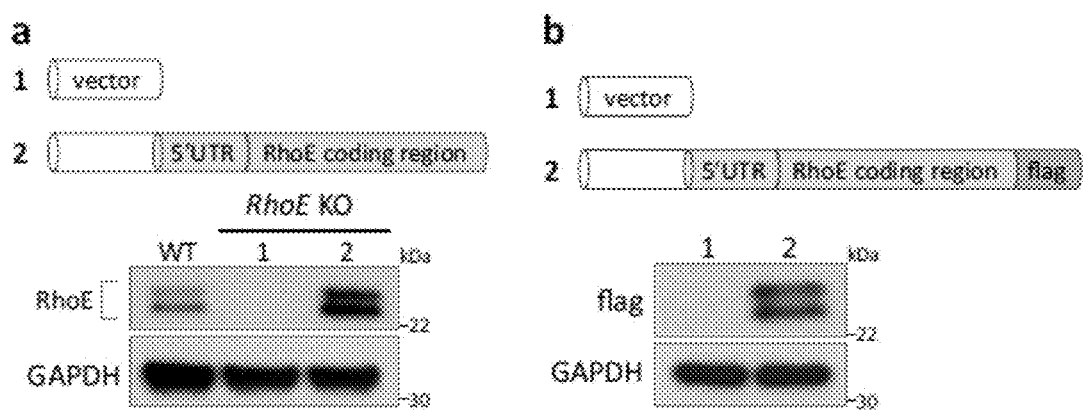
FIG. 2A-B shows A) Immunoblot for RhoE in wild-type and RhoE knockout (RhoE KO) HeLa cells transfected with either the empty vector or the RhoE expression construct. B) 5' UTR and coding region of RhoE was constructed into the C-flag vector. HeLa cells were transfected with the indicated plasmids. Cell lysates were immunoblotted for flag-tagged proteins.

To provide definitive evidence, mass spectrometry analysis was performed in two protein bands ~27 kDa immunoprecipitated by RhoE antibody (FIG. 1f). The mass sequences of the two protein bands highly matched to RhoE protein, compatible with the existence of two isoforms of RhoE. The short isoform of RhoE was translated from ATG46. Alternative translation initiation and alternative splicing from a single gene are the two major mechanisms resulting in a generation of protein isoform in most circumstances (Bazykin 2011; Kochetov 2008; Modrek 2001; Modrek 2002). To determine whether these mechanisms are responsible for existence of the additional RhoE protein band, RhoE knockout cell line was generated by the CRISPR technique in HeLa cells, and then an expression vector containing human RhoE 5' untranslated region (UTR) and coding sequence was transiently transfected into this cell line. The expression of both RhoE and the additional band in the transient transfection cells (FIG. 2a) was detected. Molecular weights of the two proteins were consistent with endogenous RhoE immunoblot bands (FIG. 2a). The result was further confirmed by a second expression vector containing the same human RhoE cDNA sequence fused with a flag tag. Two protein bands of RhoE were shown again by immunoblot using anti-flag antibody (FIG. 2b). Since the expression of two RhoE proteins directly came from the expression vector, the result ruled out the possibility of alternative splicing mechanism responsible for this undefined protein.

To examine whether alternative translation initiation generates this additional RhoE-like protein, we looked for possible alternative translation initiation site (aTIS) in RhoE gene. The first strategy used was inserting a translation stop codon immediately before and after the currently known RhoE TIS called ATG1, respectively, in human RhoE expression vector (FIG. 3a, left panel). The expression of RhoE by these two expression vectors was analyzed by western blot. It was found that insertion of stop codon before ATG1 showed no effect on the expression of both RhoE proteins (FIG. 3a, right panel lane 3), indicating that 5'UTR of RhoE did not harbor any alternative translation start site.

Although insertion of the stop codon after ATG1 eliminated the upper protein band (FIG. 3a, right panel lane 4), which is the known RhoE protein, the lower band still existed. The result clearly indicates the existence of a new RhoE isoform and translation of this isoform starts downstream of ATG1. To distinguish these two proteins, the new isoform of RhoE was designated as RhoEα. Human RhoE mRNA coding region was then analyzed, and five additional ATG codons were found in-frame with ATG1. They were ATG46, ATG388, ATG493, ATG658, and ATG730 (FIG. 3b). Among them, only ATG46 was possible to encode a protein with a molecular weight close to the detected band. This was tested by mutating ATG1 and ATG46, respectively, in RhoE expression vector (FIG. 3c). Again, mutation of ATG1 to AAA resulted in a loss of the RhoE protein expression (FIG. 3c, right panel lane 3). The replacement of ATG46 with AAA, however, eliminated RhoEα protein expression (FIG. 3c, right panel lane 4), further confirming this.

To demonstrate the result in ex vivo, ATG1 and ATG46 were deleted in RhoE genome via CRISPR-mediated point mutation technique in HeLa cells (FIG. 3d). Again, the result was consistent with the above in vitro observation, strongly supporting ATG1 and ATG46 as the TIS responsible for RhoE and RhoEα expression, respectively.

Figure 6:
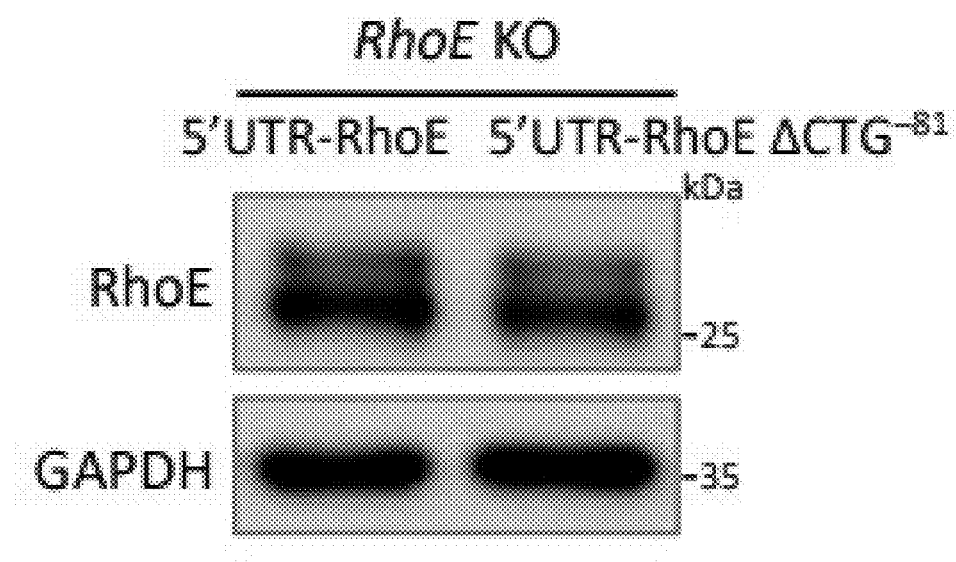
FIG. 6 shows predicted aTIS in RhoE 5'UTR is not responsible for new RhoE isoform expression. RhoE knockout (RhoE KO) HeLa cells were transfected with the indicated expression plasmids and cell lysates were immunoblotted for RhoE.

It was noticed that a computer-predicted aTIS, CTG-81, at the 5' UTR of RhoE was reported (Wan 2014). It was examined and aTIS and it was found that the expression of RhoEα was not interfered after deletion of this presumed aTIS (FIG. 6). Collectively, these data uncover RhoEα as a 15 amino acids shorter isoform of RhoE. A second TIS ATG46 in RhoE coding region, but not alternative splicing, is responsible for RhoEα expression.

It is intriguing to realize that a potent Kozak sequence is around ATG46, while the ATG1 has less optimal Kozak sequence (FIG. 3e). These results show that an optimal context around the second AUG can trigger 40 S ribosomal subunits to initiate translation (Kozak 1991). Finally, a highly conserved ATG46 among vertebrate species is observed, suggesting a broad existence of RhoEα expression across species (FIG. 3f). The result also rules out a possibility of mobility shift caused by a posttranslational modification (PTM)33.

Figure 4:
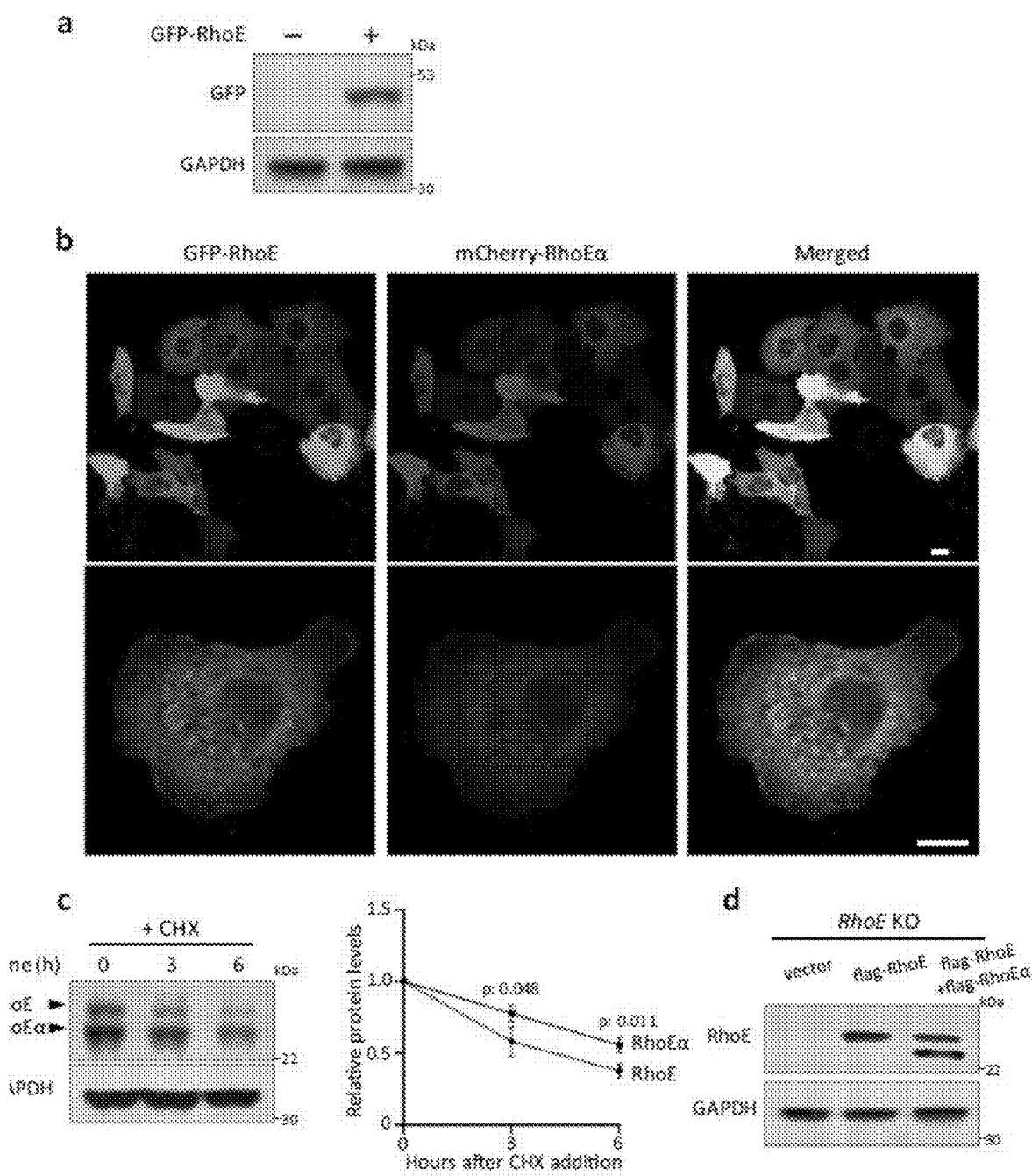
FIG. 4A-D shows A) Immunoblot showed expression of only RhoE, but not RhoEα from the GFP-RhoE expression plasmid. B) Confocal images exhibited subcellular localizations of GFP-RhoE and mCherry-RhoEα in the transfected HeLa cells. Scale bar: 10 µm. C) Immunoblot analysis showed the degradation of RhoE and RhoEα along with time in HeLa cells. Cycloheximide (CHX) 20 µg/ml was used to inhibit protein synthesis. Protein levels of RhoE and RhoEα were normalized to GAPDH, and three independent experiments were pooled and quantified (right panel). D) Indicated plasmids were transfected into RhoE knockout (RhoE KO) HEK293 cells. Cell lysates were immunoblotted for RhoE.
Figure 7:
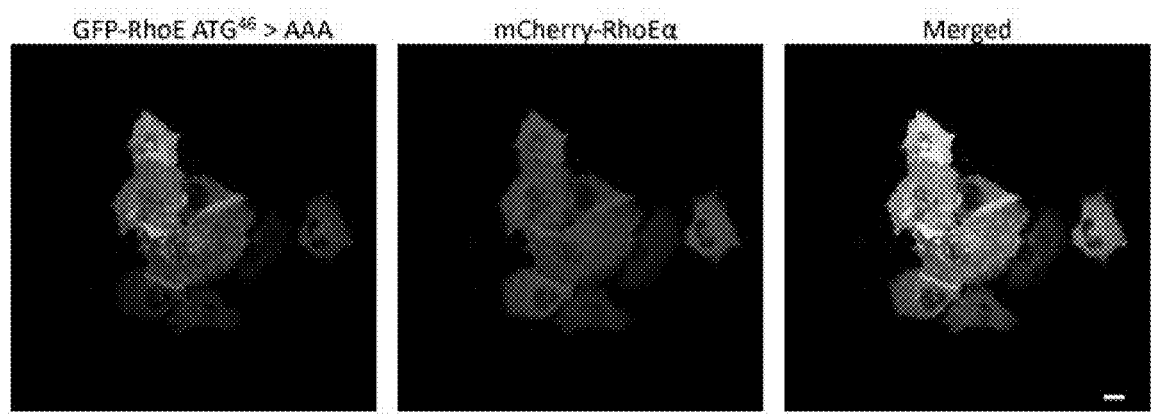
FIG. 7 shows confocal images exhibited subcellular localizations of GFP-RhoE with ATG46 to AAA mutation and mCherry-RhoEα in HeLa cells. Scale bar: 10 µm.

Localization and protein stability between RhoE and RhoEα. The characteristics of RhoEcα protein were investigated. Protein localization is important for protein functions and activities, and RhoE has been reported to localize in the cytosol, plasma membrane, and internal membranes (Forster 1996; Guasch 1998). The two proteins' cellular localization were compared by co-transfection of GFP-RhoE and mCherry-RhoEα expression vectors. GFP-RhoE expression vector was validated by western blot to ensure the expression of RhoE only, but not RhoEα (FIG. 4a). Fluorescent images showed that RhoEα shared similar subcellular distribution with RhoE (FIG. 4b), showing that missing the first 15 amino acids of N-terminus of RhoE has a minimal effect on the subcellular localization of RhoEα in a normal situation. To further confirm this observation, the cellular localization of GFPRhoE ATG46>AAA mutant was compared to the localization of RhoEα protein expressed by mCherry-RhoEα. Again, the result is consistent and supports the conclusion (FIG. 7).

A higher expression level of RhoEα was observed compared to RhoE in tissues and cells (FIG. 1), which led to an evaluation of the difference in their protein stability. Cycloheximide (CHX) chase analysis was conducted, and it was found that RhoEα exhibited significantly longer half-life than RhoE (FIG. 4c), consistent with the observed high expression level of RhoEα. The different protein stability between two isoforms indicates potential distinct mechanisms in the two protein degradations. To rule out if there is any direct effort of RhoEα on the expression of RhoE or RhoE protein stability, RhoEα was reintroduced in the cells and assessed the level of RhoE protein by western blot. It was found that forced expression of RhoEα had a minimal impact on RhoE protein level (FIG. 4d).

Figure 5:
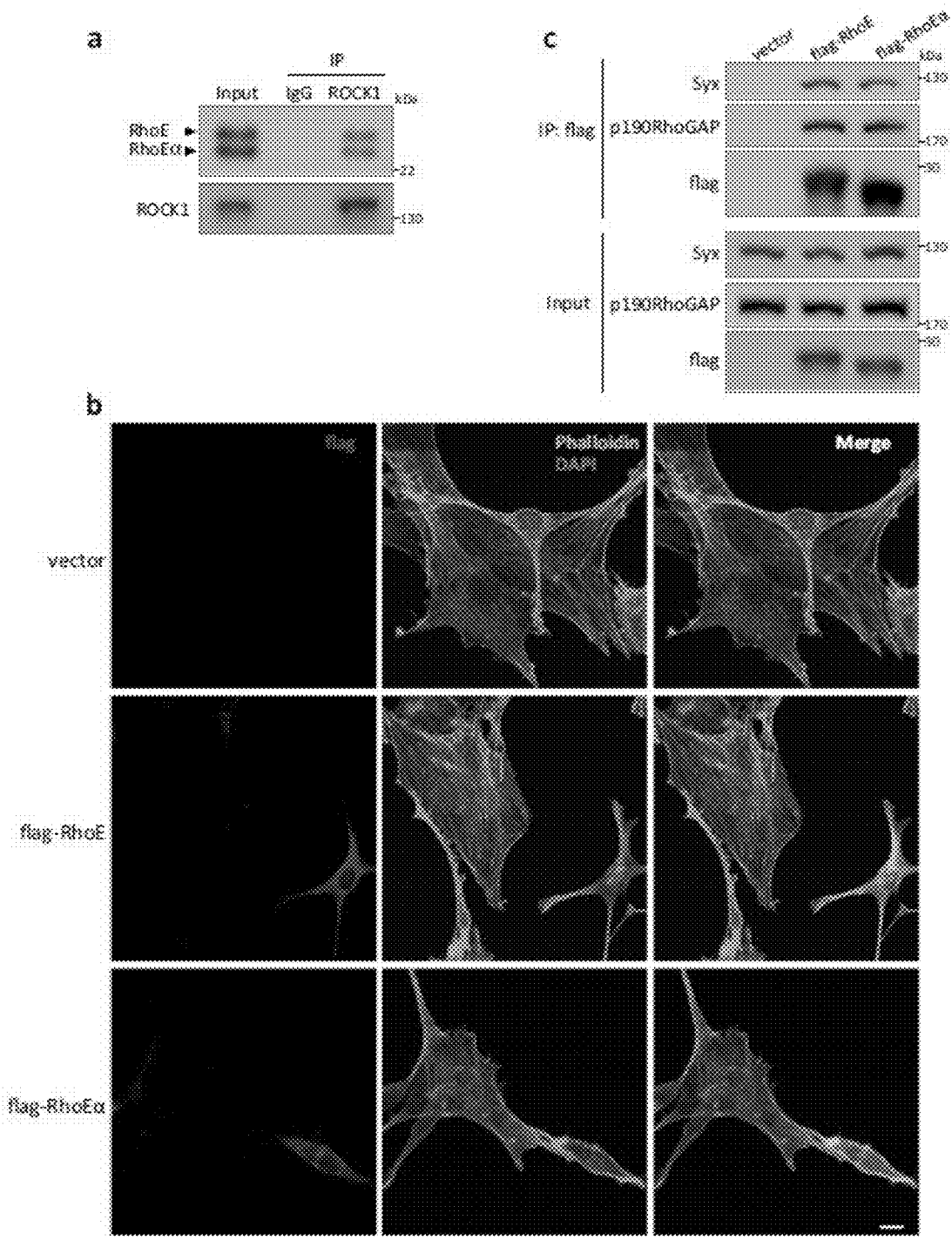
FIG. 5A-C shows A) Co-IP assay detected binding of ROCK1 to both RhoE and RhoEα in HEK293 cells. B) Confocal images of NIH-3T3 cells. Cells were transfected with the indicated plasmids and fixed 24 hours after transfection. Flag-tagged proteins were stained with anti-flag antibody. Cytoskeleton actins were stained by phalloidin. Cell nuclei was stained by DAPI. Scale bar: 10 µm. C) Co-IP assay detected binding of both RhoE and RhoEα to Syx and p190RhoGAP. HEK293 cells were transfected with indicated plasmids. Twenty four hours after transfection, cell lysates were used for Co-IP assay with anti-flag antibody.

Functional similarity and divergence between RhoE and RhoEα. RhoE was originally found to associate with RhoA/ROCK1 signaling as an antagonist, and led to an altered cell morphology to "round" shape due to the inhibition of actin cytoskeletal assembly (Jie 2015; Guasch 1998). It was investigated whether RhoEα plays a similar regulatory role in RhoA/ROCK1 signaling through interacting with ROCK1. A co-IP assay was performed, and showed that ROCK1 bound to both RhoE and RhoEα (FIG. 5a). The binding affinity of ROCK1 to the two isoforms was comparable. The effect of RhoEα on cell actin assembly was examined. Disrupted cytoskeleton actin filaments were obviously exhibited in both RhoEα and RhoE-transfected cells, resulting in a much small cell size (FIG. 5b).

RhoE often exerts its functions through interacting with other effectors as well. The interaction of the isoforms were tested with two additional well-known RhoE effectors, p190RhoGAP and synectin-binding RhoA exchange factor (Syx), which were involved in the regulation of cell protrusion and migration (Arthur 2001), and embryonic cell shape (Goh 2006), respectively. Again, the co-IP assays indicated that RhoE and RhoEα bound to the two effectors (FIG. 5c), suggesting a possible functional redundancy of the two isoforms.

Considering recently unrevealed diverse functions of RhoE4 (Chardin 2006 gene expression profiles and the associated pathways in two proteins were compared, using unbiased approaches. Two cell lines with a RhoE null background were established in HEK 293 and HeLa cells, respectively, via CRISPR-mediated RhoE gene knockout. The two cell lines were chosen due to their wide applications in a broad spectrum of cell biology and cancer research. RhoE and RhoEα were then reintroduced individually into the RhoE null cell lines, by transient transfection followed by RNA-seq analysis 24 hours after transient transfection. RNA-seq data from RhoE null cells were used as a control for the analysis. The efficacy and fidelity of expression of RhoE and RhoEα were validated by western blot. RhoEα protein was exclusively expressed by flag-RhoEα, but not flag-RhoE expression vector (FIGS. 8A and 9A).

Figure 8:
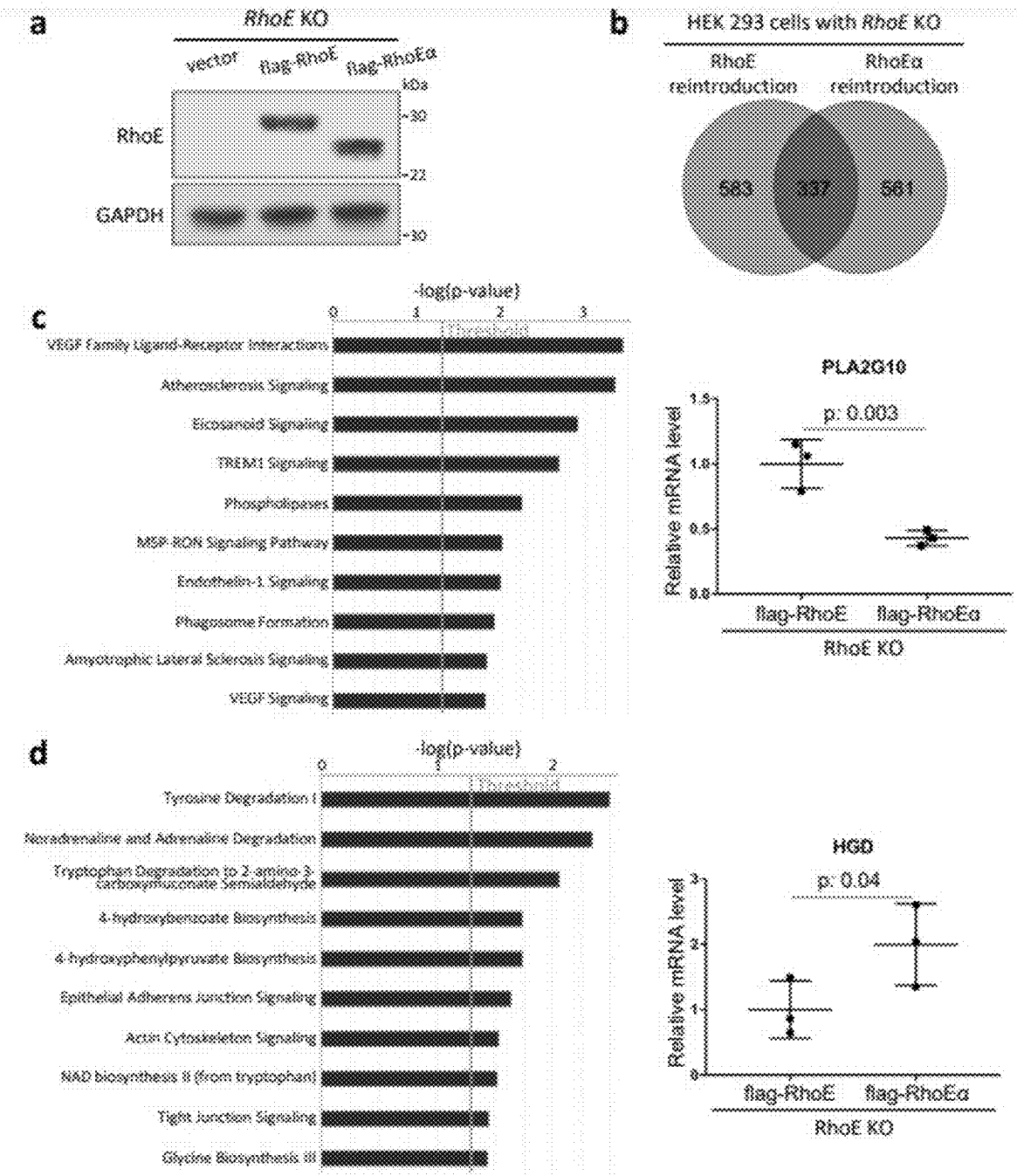
FIG. 8A-D shows transcriptomes differentially regulated by RhoE and RhoEα in HEK 293 cells. HEK 293 cells with RhoE knockout (RhoE KO) were transfected with flag-RhoE or flag-RhoEα expression plasmid individually. A) Indicated expression plasmids were validated by immunoblot analysis in the transfected RhoE KO HEK 293 cells. B) RNA-Seq was performed before and after transfection. RhoE re-introduction led to 920 genes change>2-fold and RhoEα re-introduction led to 898 genes change>2-fold. 337 genes were overlapped between two groups. C) IPA analysis of the 583 genes regulated only by RhoE, and D) the 561 genes regulated only by RhoEα. Differential expression levels of genes in top changed pathway were validated by RT-qPCR. PLA2G10 and HGD were chosen for the assessment (right panels of c and d). n=3.

It was found that introduction of RhoE and RhoEα resulted in obvious changes in 920 and 898 genes (more than twofold), respectively, in the HEK 293 cell line (FIG. 8A-B). Among them, about two-third of gene expressions were uniquely induced by the introduction of two isoforms (583 and 561, respectively). Ingenuity pathway analysis (IPA) was performed in the two unique sets of genes and we observed a distinct difference in the general canonical pathways. Of note, RhoE was closely involved in VEGF-related pathways, consistent with a previous report on the regulatory role of RhoE in responsive cardiac angiogenesis16. RhoEα was associated with metabolism pathways, such as tyrosine degradation, noradrenaline and adrenaline degradation, and tryptophan degradation to 2-amino-3-carboxymuconate semialdehyde, etc. The differential expression levels among genes between RhoE and RhoEα group were validated by RT-qPCR, and phospholipase A2 group 10 (PLA2G10) and homogentisate 1,2-dioxygenase (HGD) were chosen for the assessment (right panels in FIG. 8C-D).

Figure 9:
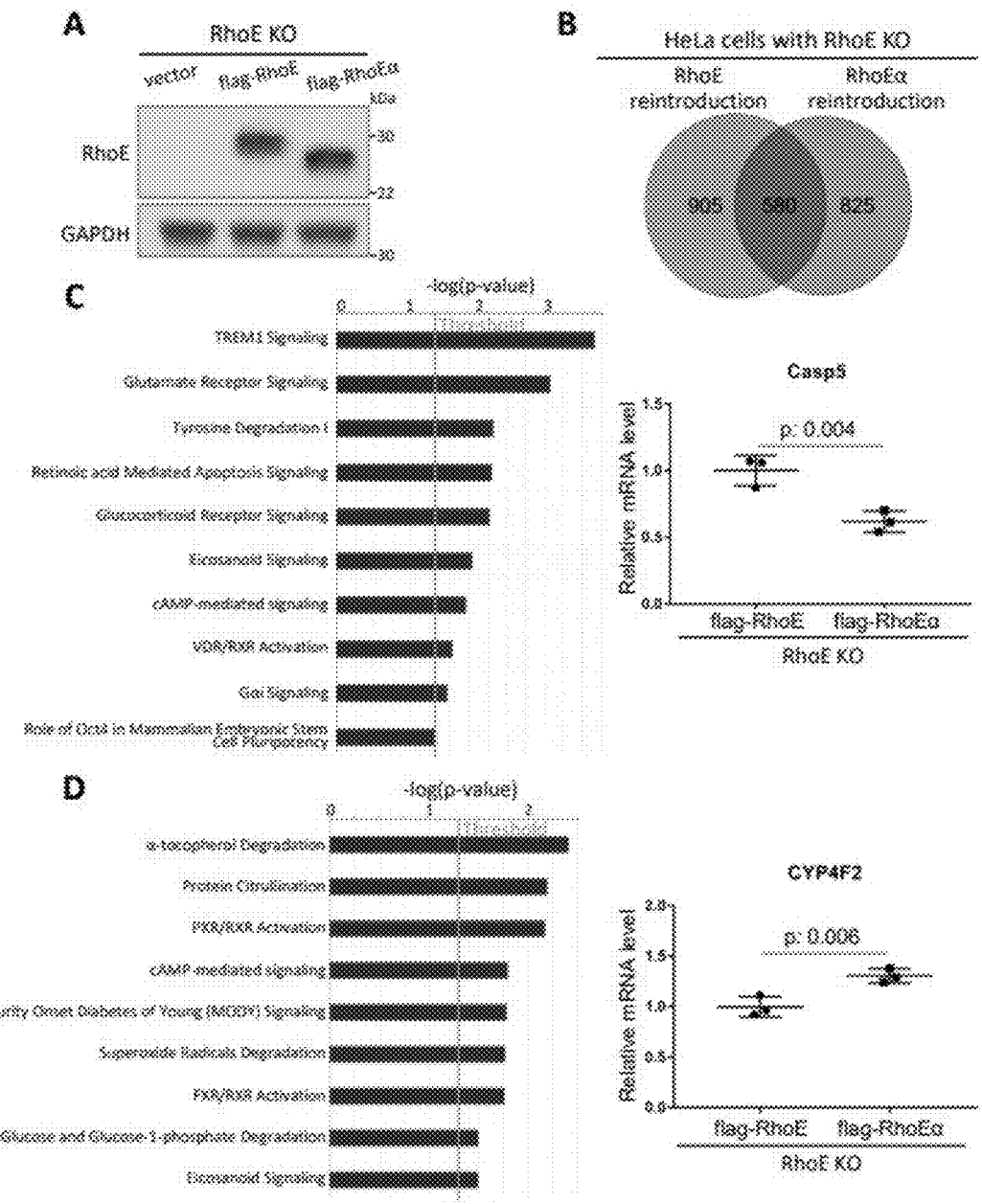
FIG. 9A-D shows transcriptomes differentially regulated by RhoE and RhoEα in HeLa cells. HeLa cells with RhoE knockout (RhoE KO) were transfected with flag-RhoE or flag-RhoEα plasmid individually. A) Indicated expression plasmids were validated by immunoblot analysis in the transfected RhoE KO HeLa cells. B) RNA-Seq was performed before and after transfection. RhoE re-introduction led to 1485 genes change>2-fold and RhoEα re-introduction led to 1405 genes change>2-fold. 580 genes were overlapped between two groups. C) IPA analysis of the 905 genes regulated only by RhoE, and D) the 825 genes regulated only by RhoEα. Differential expression levels of genes in top changed pathway were validated by RT-qPCR. Casp5 and CYP4F2 were chosen for the assessment (right panels of c and d). n=3.

Using the same strategy, the gene expression profiles in the HeLa cell line were analyzed after the introduction of the two RhoE isoforms (FIG. 9A). The re-expression of RhoE and RhoEα led to 1485 and 1405 gene transcript changes in more than twofold, respectively. The expression pattern induced by the two isoforms was similar to the observation detected in the HEK 293 cell line. Among the 1485 genes altered by RhoE, only 580 genes were overlapped with the genes induced by RhoEα (FIG. 9A-B). Moreover, 905 and 825 genes were specifically induced by RhoE and RhoEα, respectively. IPA analysis of these specifically induced genes revealed cross talk, as well as distinct pathways (FIG.

9C-D). Both RhoE and RhoEα were associated with tyrosine degradation, retinoid X receptor activation, eicosanoid signaling, and cAMP-mediated signaling. Meanwhile, RhoE showed a strong connection to TREM1 signaling and glutamate receptor signaling, while RhoEα seemed associated with protein citrullination. The differential expression levels among genes between RhoE and RhoEα group were validated by RT-qPCR and caspase 5 (Casp5) and leukotriene-B(4) omega-hydroxylase 1 (CYP4F2) were chosen for the assessment (FIG. 9C-D).

DISCUSSION

RhoE is a small GTPase universally expressed in tissues and organs, and has shown diverse biological functions (Jie 2015; Chardin 2006). Animal studies have demonstrated that general RhoE gene deletion in mouse led to early embryonic lethality due to fetal arrhythmias (Yang 2015) Abnormal neuron development, hydrocephalus, myocardial apoptosis and inflammation, and tumor growth and metastasis have also been linked to the downregulation of RhoE (Yue 2014; Yue 2016; Dai 2019; Paysan 2016; Chardin 2006; Pacary 2011). Despite such diverse and critical functions of RhoE, regulation of RhoE expression and activity has remained elusive and most studies have been focused on the regulatory effects of RhoE protein by PTMs, such as phosphorylation and farnesylation (Riento 2005; Riou 2013) and microRNAs (Xia 2010; Luo 2012; Chang 2014; Jiang 2020). Disclosed herein is the finding that RhoEα is a new RhoE isoform, and its existence is demonstrated in both tissues and multiple cell lines. RhoEα and RhoE share a similar expression pattern, subcellular distribution, and binding capacity to downstream effector ROCK1, p190RhoGAP, and Syx in physiological conditions. We further find that RhoEα protein exhibits a longer half-life and divergent regulatory pathways compared to RhoE. The similar and differential functions of RhoEα can explain how the fundamental and diverse functions are achieved by this small GTPase. The discovery expands the scope of small GTPases and there may exist isoforms of other GTPases in such a manner.

Protein synthesis, or translation of mRNA into amino acids, represents the final stage in the flow of genetic information. More than a simple assembly platform, recent studies have uncovered the critical regulatory role of the translation process both in manipulating protein expression and expanding proteome diversity (Jackson 2010; Kozak 1999). Growing evidence shows that the translation machinery has great hidden coding potential, and can selectively initiate translation upstream and/or downstream of the annotated coding sequence (Calvo 2009; Ingolia 2009). Of note, one screening study in global translation initiation has reported 6991 possible aTIS in 4961 human genes and 9973 aTIS in 5668 mouse genes (Wan 2014). Among these predicted aTIS, there is one at the 5' UTR of RhoE in the database. Interestingly, this study has excluded this presumed aTIS, since the insertion of a stop codon at the end of RhoE 5' UTR has shown no effect on either RhoE or RhoEα expression. Instead, ATG46, an aTIS downstream of the canonical translational start site ATG1, was identified as being responsible for the expression of RhoEα. Individual mutation of ATG1 and ATG46 at the RhoE coding sequence diminishes the expression of RhoE and RhoEα, respectively, showing that continual identification and validation of these new translational products by bench experiments are critically important.

PTM, i.e., phosphorylation, can cause unpredictable changes to protein electrophoretic mobility (Shirai 2008; Shi 2012). Madigan et al. observed phosphorylation of RhoE upon PKC agonist stimulation, which led to an electrophoretic mobility shift of exogenously expressed RhoE (Madigan 2009). Though band shift of RhoE occurs after phosphorylation and other possible types of PTM, the extra RhoE band identified in this study is clearly derived from the alternative translation. Protein expression analysis with the ATG1 and ATG46 point mutations demonstrates that the upper band is RhoE, while the short isoform RhoEα is derived from alternative translational site ATG46. Obviously, as the function and localization of RhoE are tightly regulated by phosphorylation and farnesylation, correlated PTM studies of RhoEα should further expand knowledge about this new RhoE isoform.

Figure 10:
FIG. 10 shows RhoE protein secondary structure analysis. RhoE full length was assessed in the Phyre2 web portal and no secondary structures were suggested within the first 21 amino acids of RhoE. The sequence shown is represented by SEQ ID NO: 21.

RhoE localizes in both cell cytosol and membrane to mediate its regulatory roles (Foster 1996; Guasch 1998). The fluorescent images show that RhoEα exhibits a similar localization pattern with RhoE in normal cell culture conditions, indicating that the first 15 amino acids in the N-terminus of RhoE may not contribute to its subcellular localization. The result is consistent with the protein structure prediction (FIG. 10) and the crystal structure study of RhoE (Fiegen 2002), which showed the absence of secondary structures within the first 21 amino acids in RhoE's N-terminus. Meanwhile, given the fact of the dynamic movement of RhoE between cytosol and cell membrane during important biological processes, such as membrane blebbing, cell rounding, and migration (Azzarelli 2014; Aoki 2016; McColl 2016), understanding the role of RhoEα in these biological processes becomes equally important.

Another interesting observation is that expression levels of the two proteins are not always equal. A higher expression level of RhoEα is often detected. In this study, it has been demonstrated that RhoEα is more stable with a longer half-life than RhoE, which partially explained the unequal expression levels of the two isoforms. The possibility of RhoEα-mediated degradation of RhoE was also eliminated. Meanwhile, a bioinformatic analysis revealed a strong Kozak sequence around ATG46 compared to the one near ATG1, which can contribute to the varying levels of the two proteins. Goh et al. reported that RhoE can be stabilized by its effectors, such as Syx and p190RhoGAP (Goh 2012). That result was repeated on RhoEα and it was further found that RhoEα was also able to interact with the two effectors, with similar binding affinities compared to RhoE. The increased protein stability of RhoEα indicates the possibility of uncovered RhoEα-specific effectors that can enhance RhoEα stability or inhibit its degradation.

While the major discovery of the study was the identification and characterization of a new isoform RhoEα, several basic studies on the function of RhoEα were explored. The results indicated functional similarity between the two isoforms, which included physical interactions with ROCK1, p190RhoGAP, Syx, and the inhibitory effect on actin assembly.

Finally, the differential transcriptome profiles and the associated signaling pathways were compared between RhoE and RhoEα in two cell lines. The data indicate that one-third of genes are commonly regulated by the two proteins, and the remaining are differentially regulated by RhoE and RhoEα individually. The IPA revealed some consistent, as well as distinct signaling pathways associated with the two proteins. For an example, VEGF, inflammation, and cAMP-mediated signaling have been reported previously (Yang 2015; Yue 2014; Yue 2016).

Methods

Animals. Tissues were collected from male C57BL/6 mice at the age of 10 weeks. RhoE null MEF cells were isolated from RhoE null (RhoE−/−) mice 14. All animal experiments were approved by the Institutional Animal Care and Use Committee of Texas A&M University College of Medicine, Institute of Biosciences and Technology.

siRNAs, plasmids, oligos, and antibodies. Nontargeting siRNA (D-001810-01-05), human SMARTpool RhoE siRNA (L-007794-00-0005), and mouse SMARTpool RhoE siRNA (L-064484-01-00005) were from GE Dharmacon. Restriction enzyme-based cloning was used for plasmid construction. For 5' UTR-RhoE and 5' UTR-RhoE-flag constructs, 5' UTR and coding sequence of RhoE cDNA (ENST00000263895.8) was amplified by PCR from HeLa cell cDNA library, and inserted into pcDNA3.1 and CMV—COOH-3xflag vector. For flag-RhoE and GFPRhoE constructs, human RhoE coding sequence was inserted into CMV-NH2-3xflag and pEGFP-C3 vector. For flag-RhoEα and mCherry-RhoEα, human RhoE coding region starting from ATG46 was inserted into CMV-NH2-3xflag and pmCherry-C1 vector. Plasmids with point mutation were constructed using the Q5 site-directed mutagenesis kit (NEB, E0554S). Oligos used for RT-qPCR included:

```
PLA2G10:
                           (SEQ ID NO: 25)
GGTTGCTTTTGTGGCTTGGGAG (SEQ ID NO: 26)
GATTGACGCACTGCCAGGAGTA

HGD:
                           (SEQ ID NO: 27)
CATCTTGGAGGTCTATGGTGTCC (SEQ ID NO: 28)
GACCGTGTAACCACCTGGTACT

Casp5:
                           (SEQ ID NO: 29)
ACAACCGCAACTGCCTCAGTCT (SEQ ID NO: 30)
GAATCTGCCTCCAGGTTCTCAG

CYP4F2:
                           (SEQ ID NO: 31)
GACAGCCATTGTCAGGAGAAACC (SEQ ID NO: 32)
TGCAGGAGGATCTCATGGTGTC
```

The antibodies used in the study included: RhoE (EMD Millipore, 05-723, LOT: 2802018), GAPDH (Cell Signaling Technology, #5174), flag (Sigma Aldrich, F1804-1MG), ROCK1 (Santa Cruz Biotechnology, sc-5560), Syx (ThermoFisher Scientific, PA5-62010), p190RhoGAP (Santa Cruz Biotechnology, sc-393241), anti-mouse IgG HRP-linked secondary antibody (Cell Signaling Technology, #7076), anti-rabbit IgG HRP-linked secondary antibody (Cell Signaling Technology, #7074), conformation-specific anti-mouse IgG HRP-linked secondary antibody (Abcam, ab131368), and conformation-specific anti-rabbit IgG HRP-linked secondary antibody (Cell Signaling Technology, #5127).

Mass spectrometry. HEK 293 cell lysate was subjected to anti-RhoE antibody pull-down followed by SDS-PAGE gel separation. The gel was stained with 0.1% Coomassie brilliant blue R250 and two bands ~27 kDa were excised. The samples were digested by trypsin. The mass spectrometry analysis was performed by the Mass Spectrometry Facility at the University of Texas Medical Branch at Galveston using SCIEX TOF/TOF 5800 system.

CRISPR-mediated genome editing. The CRISPR-mediated genomic deletion was performed as described previously57. For RhoE deletion in HeLa and HEK 293 cells, guide RNA (GGGCGGACATTGTCATAGTA, SEQ ID NO: 37) specifically targeting on RhoE exon 4 was cloned into pSpCas9(BB)-2A-Puro (PX459) V2.0 (Addgene, #62988). Cells were transfected with the fused plasmid by lipofectamine 2000. Two days after transfection, the cells were treated with puromycin at 2.5 µg/ml for 3 days. Puromycin-resistant cells were harvested and further seeded into a 96-well plate, using a serial dilution for single-cell clones. Cell clones were validated by immunoblot. For CRISPR-mediated activation of RhoE promoter, HeLa cells were transfected with the Cas9-SAM components, including dCas9-VP64-GFP (Addgene, #61422), MS2-P65-HSFI-GFP (Addgene, #61423), and sgRNA(MS2) cloning vector (Addgene, #61424) fused with guide RNA (ATCTGCCTCCTCCCCTTTTA. SEQ ID NO: 33) targeting on human RhoE promoter region. For CRISPR-mediated genomic point mutation, guide RNA (TTTGCTGGATAATTTCTGGC, SEQ ID NO: 34) targeting on RhoE exon 2 was cloned into pSpCas9(BB)-2A-Puro (PX459) V2.0. The single-stranded donor oligonucleotide (ssODN) designed as repair template to create ATG1 deletion mutation is CACACTGACTGTCTCC-CACCACAACTATCT TGCATTTCACGTTCTGATTAG-GATCCATGATAGATTTGCTGGATAATTTCTGG CTTGCTC TTCTCTCCTTTGATGTTGCCTTAT-TTTCTCTTGGAACAGGAATTTTCTCTTAAGAAG (SEQ ID NO: 35). The ssODN as repair template to create ATG46 deletion mutation is CACACTGACTGTCTCC-CACCACAACTATCTTGCATTTCACGTTCTGATTAG-GATCGATA GATTTGCTGGATAATTTCTGGCTT GCTCTTCTCTCCTTCATTGATGTTGCCTTATTTTCTC TTGGAACAGGAATTTTCTCTTAAGAAG (SEQ ID NO: 36). HeLa cells were co-transfected with the sgRNA/Cas9 containing plasmid and the ssODN. Two days after transfection, the cells were treated with puromycin at 2.5 µg/ml for three days. Puromycin-resistant cells were subjected to immunoblot assay.

Immunofluorescent staining and fluorescent imaging. NIH-3T3 cells were cultured in a 35-mm culture dish (MatTek, P35G-1.5-14-C) for overnight and then transfected with three expression vectors control, flag-RhoE and flag-RhoEα individually. Twenty four hours after the transfection, cells were washed and fixed by 4% paraformaldehyde for 30 min. The cells were probed by the anti-flag antibody (Sigma Aldrich, F1804-1MG) followed by the second antibody, Alexa Fluor 594 goat anti-mouse IgG (ThermoFisher Scientific, A-11005). Alexa Fluor 488 Phalloidin (ThermoFisher Scientific, A12379) was used for cytoskeleton actin staining. For fluorescent imaging analysis, HeLa cells were co-transfected with GFP-RhoE and mCherry-RhoEα plasmids. Imaging was taken by Nikon Confocal A1 laser microscope.

Cycloheximide chase assay. The degradation of RhoE and RhoEα was analyzed by CHX chase assay. HeLa cells were seeded in a six-well plate, incubated overnight, and subsequently treated with 20 µg/ml CHX for 0, 3, and 6 hours, respectively. Cell lysates were then collected and subjected to immunoblotting assay for detection of RhoE and RhoEα levels. Immunoblots were qualified by densitometry of the film using ImageJ software. Three independent experiments were performed, and the data were analyzed by the associated statistical analysis.

RNA sequencing. RNA was isolated from HEK 293 cells and HeLa cells using TRIzol reagent. For each sample, a total of 10 μg RNA was used for mRNA purification and cDNA library preparation according to the Ultra Directional RNA Library Prep Kit for Illumina (NEB, E7420S). The quality control of the library quality control was assessed by Qubit (Thermo Fisher) and qPCR. The libraries were sequenced using an Illumina Novaseq 6000 platform with paired-end 150 bp strategy. The quality of raw RNA-sequencing data was validated by the FastQC software. The sequencing reads were aligned to hg38 using Tophat and the reads mapping to each of the 56,269 genes/locations were counted using HTSeq. R package DESeq was used to normalize and generate the variance of stabilizing transformation data. The fold changes were calculated for differential gene expression analysis. IPA was used to analyze the differentially expressed genes with |fold change|≥2. The raw RNA-seq data were deposited in the Gene Expression Omnibus (GEO) with accession number GSE132718.

Statistics and reproducibility. For two-group comparisons, unpaired student's t test was used. A value of $p<0.05$ was considered statistically significant. For protein stability assay, the experiment was independently replicated three times and the results were qualified together. Experiments and data assessment were conducted double blinded by investigators.

The compositions, devices, systems, and methods of the appended claims are not limited in scope by the specific compositions, devices, systems, and methods described herein, which are intended as illustrations of a few aspects of the claims. Any compositions, devices, systems, and methods that are functionally equivalent are intended to fall within the scope of the claims. Various modifications of the compositions, devices, systems, and methods in addition to those shown and described herein are intended to fall within the scope of the appended claims. Further, while only certain representative compositions, devices, systems, and method steps disclosed herein are specifically described, other combinations of the compositions, devices, systems, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

Unless defined otherwise, all technical and scientific terms used herein have the same meanings as commonly understood by one of skill in the art to which the disclosed invention belongs. Publications cited herein and the materials for which they are cited are specifically incorporated by reference.

REFERENCES

1. Boureux, A., Vignal, E., Faure, S. & Fort, P. Evolution of the Rho family of raslike GTPases in eukaryotes. Mol. Biol. Evol. 24, 203-216 (2007).
2. Lawson, C. D. & Ridley, A. J. Rho GTPase signaling complexes in cell migration and invasion. J. Cell Biol. 217, 447-457 (2018).
3. Hodge, R. G. & Ridley, A. J. Regulating Rho GTPases and their regulators. Nat. Rev. Mol. Cell Biol. 17, 496-510 (2016).
4. Jie, W. et al. Pathophysiological functions of Rnd3/RhoE. Compr. Physiol. 6, 169-186 (2015).
5. Dai, Y., Luo, W. & Chang, J. Rho kinase signaling and cardiac physiology. Curr. Opin. Physiol. 1, 14-20 (2018).
6. Foster, R. et al. Identification of a novel human Rho protein with unusual properties: GTPase deficiency and in vivo farnesylation. Mol. Cell Biol. 16, 2689-2699 (1996).
7. Guasch, R. M., Scambler, P., Jones, G. E. & Ridley, A. J. RhoE regulates actin cytoskeleton organization and cell migration. Mol. Cell Biol. 18, 4761-4771 (1998).
8. Riento, K. & Ridley, A. J. Rocks: multifunctional kinases in cell behaviour. Nat. Rev. Mol. Cell Biol. 4, 446-456 (2003).
9. Riento, K., Guasch, R. M., Garg, R., Jin, B. & Ridley, A. J. RhoE binds to ROCK I and inhibits downstream signaling. Mol. Cell Biol. 23, 4219-4229 (2003).
10. Ongusaha, P. P. et al. RhoE is a pro-survival p53 target gene that inhibits ROCK I-mediated apoptosis in response to genotoxic stress. Curr. Biol. 16, 2466-2472 (2006).
11. Villalonga, P., Guasch, R. M., Riento, K. & Ridley, A. J. RhoE inhibits cell cycle progression and Ras-induced transformation. Mol. Cell Biol. 24, 7829-7840 (2004).
12. Maekawa, M. et al. Signaling from Rho to the actin cytoskeleton through protein kinases ROCK and LIM-kinase. Science 285, 895-898 (1999).
13. Arber, S. et al. Regulation of actin dynamics through phosphorylation of cofilin by LIM-kinase. Nature 393, 805-809 (1998).
14. Yang, X. et al. Genetic deletion of Rnd3/RhoE results in mouse heart calcium leakage through upregulation of protein kinase A signaling. Circulation Res. 116, e1-e10 (2015).
15. Yue, X. et al. Rnd3 haploinsufficient mice are predisposed to hemodynamic stress and develop apoptotic cardiomyopathy with heart failure. Cell Death Dis. 5, e1284 (2014).
16. Yue, X. et al. Rnd3/RhoE modulates hypoxia-inducible factor 1alpha/Vascular endothelial growth factor signaling by stabilizing hypoxia-inducible factor 1alpha and regulates responsive cardiac angiogenesis. Hypertension 67, 597-605 (2016).
17. Dai, Y. et al. RhoE fine-tunes inflammatory response in myocardial infarction. Circulation 139, 1185-1198 (2019).
18. Lin, X. et al. Genetic deletion of Rnd3 results in aqueductal stenosis leading to hydrocephalus through up-regulation of Notch signaling. Proc. Natl Acad. Sci. USA 110, 8236-8241 (2013).
19. Liu, B. et al. Downregulation of RND3/RhoE in glioblastoma patients promotes tumorigenesis through augmentation of notch transcriptional complex activity. Cancer Med. 4, 1404-1416 (2015).
20. Liu, B. et al. RND3 promotes Snail 1 protein degradation and inhibits glioblastoma cell migration and invasion. Oncotarget 7, 82411-82423 (2016).
21. Azzarelli, R. et al. An antagonistic interaction between PlexinB2 and Rnd3 controls RhoA activity and cortical neuron migration. Nat. Commun. 5, 3405 (2014).
22. Pacary, E., Azzarelli, R. & Guillemot, F. Rnd3 coordinates early steps of cortical neurogenesis through actin-dependent and -independent mechanisms. Nat. Commun. 4, 1635 (2013).
23. Zhou, J. et al. Chaperone-mediated autophagy regulates proliferation by targeting RND3 in gastric cancer. Autophagy 12, 515-528 (2016).

24. Paysan, L., Piquet, L., Saltel, F. & Moreau, V. Rnd3 in cancer: a review of the evidence for tumor promoter or suppressor. Mol. Cancer Res. 14, 1033-1044 (2016).
25. Jordan, P., Brazao, R., Boavida, M. G., Gespach, C. & Chastre, E. Cloning of a novel human Rac1b splice variant with increased expression in colorectal tumors. Oncogene 18, 6835-6839 (1999).
26. Marks, P. W. & Kwiatkowski, D. J. Genomic organization and chromosomal location of murine Cdc42. Genomics 38, 13-18 (1996).
27. Bazykin, G. A. & Kochetov, A. V. Alternative translation start sites are conserved in eukaryotic genomes. Nucleic Acids Res. 39, 567-577 (2011).
28. Kochetov, A. V. Alternative translation start sites and hidden coding potential of eukaryotic mRNAs. Bioessays 30, 683-691 (2008).
29. Modrek, B., Resch, A., Grasso, C. & Lee, C. Genome-wide detection of alternative splicing in expressed sequences of human genes. Nucleic Acids Res. 29, 2850-2859 (2001).
30. Modrek, B. & Lee, C. A genomic view of alternative splicing. Nat. Genet. 30, 13-19 (2002).
31. Wan, J. & Qian, S. B. TISdb: a database for alternative translation initiation in mammalian cells. Nucleic Acids Res. 42, D845-D850 (2014).
32. Kozak, M. Structural features in eukaryotic mRNAs that modulate the initiation of translation. J. Biol. Chem. 266, 19867-19870 (1991).
33. Madigan, J. P. et al. Regulation of Rnd3 localization and function by protein kinase C alpha-mediated phosphorylation. Biochem. J. 424, 153-161 (2009).
34. Arthur, W. T. & Burridge, K. RhoA inactivation by p190RhoGAP regulates cell spreading and migration by promoting membrane protrusion and polarity. Mol. Biol. Cell 12, 2711-2720 (2001).
35. Goh, L. L. & Manser, E. The RhoA GEF Syx is a target of Rnd3 and regulated via a Raf1-like ubiquitin-related domain. PLoS ONE 5, e12409 (2010).
36. Chardin, P. Function and regulation of Rnd proteins. Nat. Rev. Mol. Cell Biol. 7, 54-62 (2006).
37. Pacary, E. et al. Proneural transcription factors regulate different steps of cortical neuron migration through Rnd-mediated inhibition of RhoA signaling. Neuron 69, 1069-1084 (2011).
38. Riento, K. et al. RhoE function is regulated by ROCK I-mediated phosphorylation. EMBO J. 24, 1170-1180 (2005).
39. Riou, P. et al. 14-3-3 proteins interact with a hybrid prenyl-phosphorylation motif to inhibit G proteins. Cell 153, 640-653 (2013).
40. Xia, W. et al. MicroRNA-200b regulates cyclin D1 expression and promotes Sphase entry by targeting RND3 in HeLa cells. Mol. Cell Biochem. 344, 261-266 (2010).
41. Luo, H. et al. Up-regulated miR-17 promotes cell proliferation, tumour growth and cell cycle progression by targeting the RND3 tumour suppressor gene in colorectal carcinoma. Biochem. J. 442, 311-321 (2012).
42. Chang, L. et al. MicroRNA-200c regulates the sensitivity of chemotherapy of gastric cancer SGC7901/DDP cells by directly targeting RhoE. Pathol. Oncol. Res. 20, 93-98 (2014).
43. Fang, Y. N. et al. Highly expressed miR-182-5p can promote preeclampsia progression by degrading RND3 and inhibiting HTR-8/SVneo cell invasion. Eur. Rev. Med. Pharm. Sci. 22, 6583-6590 (2018).
44. Jiang, C. et al. Epstein-Barr virus miRNA BART2-5p promotes metastasis of nasopharyngeal carcinoma by suppressing RND3. Cancer Res. 80, 1957-1969 (2020).
45. Kozak, M. Initiation of translation in prokaryotes and eukaryotes. Gene 234, 187-208 (1999).
46. Jackson, R. J., Hellen, C. U. & Pestova, T. V. The mechanism of eukaryotic translation initiation and principles of its regulation. Nat. Rev. Mol. Cell Biol. 11, 113-127 (2010).
47. Calvo, S. E., Pagliarini, D. J. & Mootha, V. K. Upstream open reading frames cause widespread reduction of protein expression and are polymorphic among humans. Proc. Natl Acad. Sci. USA 106, 7507-7512 (2009).
48. Ingolia, N. T., Ghaemmaghami, S., Newman, J. R. & Weissman, J. S. Genomewide analysis in vivo of translation with nucleotide resolution using ribosome profiling. Science 324, 218-223 (2009).
49. Shirai, A. et al. Global analysis of gel mobility of proteins and its use in target identification. J. Biol. Chem. 283, 10745-10752 (2008).
50. Shi, Y. et al. Abnormal SDS-PAGE migration of cytosolic proteins can identify domains and mechanisms that control surfactant binding. Protein Sci. 21, 1197-1209 (2012).
51. Fiegen, D., Blumenstein, L., Stege, P., Vetter, I. R. & Ahmadian, M. R. Crystal structure of Rnd3/RhoE: functional implications. FEBS Lett. 525, 100-104 (2002).
52. Nan, X. et al. Single-molecule superresolution imaging allows quantitative analysis of RAF multimer formation and signaling. Proc. Natl Acad. Sci. USA 110, 18519-18524 (2013).
53. Muratcioglu, S. et al. GTP-dependent K-Ras dimerization. Structure 23, 1325-1335 (2015).
54. Aoki, K. et al. A RhoA and Rnd3 cycle regulates actin reassembly during membrane blebbing. Proc. Natl Acad. Sci. USA 113, E1863-E1871 (2016).
55. McColl, B., Garg, R., Riou, P., Riento, K. & Ridley, A. J. Rnd3-induced cell rounding requires interaction with Plexin-B2. J. Cell Sci. 129, 4046-4056 (2016).
56. Goh, L. L. & Manser, E. The GTPase-deficient Rnd proteins are stabilized by their effectors. J. Biol. Chem. 287, 31311-31320 (2012).
57. Yi, X. et al. Histone methyltransferase Setd2 is critical for the proliferation and differentiation of myoblasts. Biochim. Biophys. Acta Mol. Cell Res. 1864, 697-707 (2017).

```
SEQUENCES

Synthesized siRNA oligo.

1) SiRNA oligo #1: synthesized 21-mer with 19 bp duplex targeting the RhoEα
isoform region

5'--- GCAAAUCUAUCAUGGAUCCUA ---3' (SEQ ID NO: 1)

3 --- GUCGUUUAGAUAGUACCUAGG ---5' (SEQ ID NO: 2)
```

-continued 2) siRNA oligo #2: synthesized 21-mer with 19 bp duplex targeting the C-terminal region of RhoE
5'--- GCAGUUGCUACGGACUUACGA ---3' (SEQ ID NO: 3)

3 --- GCCGUCAACGAUGCCUGAAUG ---5' (SEQ ID NO: 4)

Synthesized DNA oligo expressing a shRNA in a vector (e.g. virus vector for gene therapy).
1) dsDNA oligo #3 expressing a shRNA*: targeting the RhoEα isoform region
5'--- CAAATCTATCATGGATCCTATCAAGAGTAGGATCCATGATAGATTTGC --- 3' (SEQ ID NO: 5)

3' CGTTTAGATAGTACCTAGGATAGTTCTCATCCTAGGTACTATCTAAACG --- 5' (SEQ ID NO: 6)

2) dsDNA oligo #4 expressing a shRNA*: targeting the C-terminal region of RhoE
5'--- CAGTTGCTACGGACTTACGATCAAGAGTCGTAAGTCCGTAGCAACTGC --- 3' (SEQ ID NO: 7)

3 --- CGTCAACGATGCCTGAATGCTAGTTCTCAGCATTCAGGCATCGTTGACG --- 5' (SEQ ID NO: 8)

OLIGO SETS 3 AND 4 WITH GENERIC LINKERS:
5' GCAAATCTATCATGGATCCTAXXXXXXXXXTAGGATCCATGATAGATTTGC --- 3' (SEQ ID NO: 9)

3' CGTTTAGATAGTACCTAGGATXXXXXXXATCCTAGGTACTATCTAAACG --- 5' (SEQ ID NO: 10)

5'--- CAGTTGCTACGGACTTACGAXXXXXXXXTCGTAAGTCCGTAGCAACTGC --- 3' (SEQ ID NO: 11)

3 --- GTCAACGATGCCTGAATGCTXXXXXXXAGCATTCAGGCATCGTTGACG --- 5' (SEQ ID NO: 12)

FIRST PART OF OLIGO SETS 3 AND 4
GCAAATCTATCATGGATCCTA (SEQ ID NO: 13)

CGTTTAGATAGTACCTAGGAT' (SEQ ID NO: 14)

GCAGTTGCTACGGACTTACGA (SEQ ID NO: 15)

CGTCAACGATGCCTGAATGCT (SEQ ID NO: 16)

SECOND PART OF OLIGO SETS 3 AND 4
TAGGATCCATGATAGATTTGC --- 3' (SEQ ID NO: 17)

ATCCTAGGTACTATCTAAACG --- 5' (SEQ ID NO: 18)

TCGTAAGTCCGTAGCAACTGC --- 3' (SEQ ID NO: 19)

AGCATTCAGGCATCGTTGACG --- 5' (SEQ ID NO: 20)

RND3;
SEQ ID NO: 21
MKERRASQKLSSKSIMDPNQNVKCKIVVVGDSQCGKTALLHVFAKDCFPENYV

PTVFENYTASFEIDTQRIELSLWDTSGSPYYDNVRPLSYPDSDAVLICFDISRPETLDSVL

KKWKGEIQEFCPNTKMLLVGCKSDLRTDVSTLVELSNHRQTPVSYDQGANMAKQIGA

ATYIECSALQSENSVRDIFHVATLACVNKTNKNVKRNKSQRATKRISHMPSRPELSAV

ATDLRKDKAKSCTVM

RhoE nucleic acid
SEQ ID NO: 22
aatgaaggagagaagagccagccagaaattatccagcaaatctatcatggatcctaatcagaacgtgaaatgcaagatagttg tggtgggagacagtcagtgtggaaaaactgcgctgctccatgtcttcgccaaggactgcttccccgagaattacgttcctacagtgtttgag aattacacggccagttttgaaatcgacacacaaagaatagagttgagcctgtgggacacttcgggttctccttactatgacaatgtccgccc cctctcttaccctgattcggatgctgtgctgatttgctttgacatcagtagaccagagaccctggacagtgtcctcaaaaagtggaaggtg aaatccaggaattttgtccaaataccaaaatgctcttggtcggctgcaagtctgatctgcggacagatgttagtacattagtagagctctcca atcacaggcagacgccagtgtcctatgaccagggggcaaatatggccaaacagattggagcagctacttatatcgaatgctcagctttac agtcggaaaatagcgtcagagacattttcacgttgccaccttggcatgtgtaaataagacaaataaaaacgttaagcggaacaaatcaca gagagccacaaagcggatttcacacatgcctagcagaccagaactctcggcagttgctacggacttacgaaaggacaaagcgaagagc tgcactgtgatgtg RhoEalpha:
SEQ ID NO: 23
MDPNQNVKCKIVVVGDSQCGKTALLHVFAKDCFPENYVPTVFENYTASFEIDT

QRIELSLWDTSGSPYYDNVRPLSYPDSDAVLICFDISRPETLDSVLKKWKGEIQEFCPNT

KMLLVGCKSDLRTDVSTLVELSNHRQTPVSYDQGANMAKQIGAATYIECSALQSENS

VRDIFHVATLACVNKTNKNVKRNKSQRATKRISHMPSRPELSAVATDLRKDKAKSCT

VM

RhoEalpha nucleic acid
SEQ ID NO: 24
Atggatcctaatcagaacgtgaaatgcaagatagttgtggtgggagacagtcagtgtggaaaaactgcgctgctccatgtctt cgccaaggactgcttccccgagaattacgttcctacagtgtttgagaattacacggccagttttgaaatcgacacacaaagaatagagttga gcctgtgggacacttcggggttctccttactatgacaatgtccgcccctctcttaccctgattcggatgctgtgctgatttgctttgacatcagt agaccagagaccctggacagtgtcctcaaaaagtggaaaggtgaaatccaggaatttttgtccaaataccaaaatgctcttggtcggctgc aagtctgatctgcggacagatgttagtacattagtagagctctccaatcacaggcagacgccagtgtcctatgaccaggggcaaatatg gccaaacagattggagcagctacttatatcgaatgctcagctttacagtcggaaaatagcgtcagagacatttttcacgttgccaccttggc atgtgtaaataagacaaataaaaacgttaagcggaacaaatcacagagagccacaaagcggatttcacacatgcctagcagaccagaac tctcggcagttgctacggacttacgaaaggacaaagcgaagagctgcactgtgatgtg

MISCELLANEOUS SEQUENCES:
SEQ ID NO: 25:
PLA2G10: GGTTGCTTTTGTGGCTTGGGAG

SEQ ID NO: 26:
GATTGACGCACTGCCAGGAGTA

SEQ ID NO: 27:
CATCTTGGAGGTCTATGGTGTCC

SEQ ID NO: 28:
GACCGTGTAACCACCTGGTACT

SEQ ID NO: 29:
Casp5: ACAACCGCAACTGCCTCAGTCT

SEQ ID NO: 30:
GAATCTGCCTCCAGGTTCTCAG

SEQ ID NO: 31:
CYP4F2: GACAGCCATTGTCAGGAGAAACC

SEQ ID NO: 32:
TGCAGGAGGATCTCATGGTGTC

SEQ ID NO: 33:
ATCTGCCTCCTCCCCTTTTA

SEQ ID NO: 34:
TTTGCTGGATAATTTCTGGC

SEQ ID NO: 35:
CACACTGACTGTCTCCCACCACAACTATCT

TGCATTTCACGTTCTGATTAGGATCCATGATAGATTTGCTGGATAATTTCTGGCTTG

CTCTTCTCTCCTTTGATGTTGCCTTATTTTCTCTTGGAACAGGAATTTTCTCTTAAGA

AG

SEQ ID NO: 36:
CACACTGACTGTCTCCCACCACAACT

ATCTTGCATTTCACGTTCTGATTAGGATCGATAGATTTGCTGGATAATTTCTGGCTT

GCTCTTCTCTCCTTCATTGATGTTGCCTTATTTTCTCTTGGAACAGGAATTTTCTCTT

AAGAAG

What is claimed is:

1. A method of inhibiting RND3 or RhoEα expression in a subject in need thereof, the method comprising administering to the subject a composition comprising an siRNA, wherein said siRNA comprises at least 90% identity to one or more of SEQ ID NOS: 1, 2, 3, or 4.

2. The method of claim 1, wherein the subject is administered a composition comprising an siRNA, wherein said siRNA comprises 90% or more identity to SEQ ID NO: 1 and further wherein the subject is also administered an siRNA comprising 90% or more identity to SEQ ID NO: 2.

3. The method of claim 1, wherein the subject is administered a composition comprising an siRNA, wherein said siRNA comprises 90% or more identity to SEQ ID NO: 3 and further wherein the subject is also administered an siRNA comprising 90% or more identity to SEQ ID NO: 4.

4. The method of claim 1, wherein the subject is administered a composition comprising an siRNA, wherein said siRNA comprises 90% or more identity to each of SEQ ID NOS: 1-4.

5. The method of claim 1, wherein the subject has a cancer comprising leukemia, prostate cancer, ovarian cancer, pancreas cancer, lung cancer, breast cancer, liver cancer, head and neck cancer, colon cancer, gastrointestinal cancers, bladder cancer, non-Hodgkin's lymphoma cancer, or melanoma.

6. The method of claim 1, wherein the composition is a pharmaceutical composition.

7. The method of claim 1, wherein the composition further comprises an adjuvant.

8. The method of claim 1, wherein the composition further comprises an additional medicament for treating the subject.

9. The method of claim 8, wherein said additional medicament is related to the treatment of an RND3-related condition.

10. The method of claim 9, wherein said additional medicament treats cancer, inflammation, or calcium homeostasis.

* * * * *